(12) United States Patent
Stanford

(10) Patent No.: US 9,150,925 B1
(45) Date of Patent: Oct. 6, 2015

(54) SNP PANELS FOR PREDICTING PROSTATE CANCER-SPECIFIC MORTALITY

(75) Inventor: Janet L. Stanford, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 636 days.

(21) Appl. No.: 12/953,261

(22) Filed: Nov. 23, 2010

Related U.S. Application Data

(60) Provisional application No. 61/264,163, filed on Nov. 24, 2009.

(51) Int. Cl.
*C12Q 1/68* (2006.01)

(52) U.S. Cl.
CPC .................................. *C12Q 1/6886* (2013.01)

(58) Field of Classification Search
None
See application file for complete search history.

(56) References Cited

U.S. PATENT DOCUMENTS

2001/0053519 A1* 12/2001 Fodor et al. .................... 435/6

OTHER PUBLICATIONS

Lui et al. (Genes, Chromosomes & Cancer 45:1018-1032 (2006)).*
NEB catalog (1998/1999), pp. 121, 284.*

* cited by examiner

*Primary Examiner* — Juliet Switzer
(74) *Attorney, Agent, or Firm* — Lowe Graham Jones; Gary M. Myles

(57) ABSTRACT

Provided are SNP panels and methods that employ SNP panels for predicting prostate cancer-specific mortality in a human patient. Exemplary SNP panels presented herein comprise one or more of the SNPs designated rs1137100, rs228697, rs2839685, rs1799814, rs627839, rs5993891, rs635261, rs11710277, rs11205, rs2494750, rs4608577, rs4645959, rs1799964, rs25487, rs2308327, rs915927, rs2070874, rs1029153, rs12467911, rs10778534, rs523349, and rs4583514 and are exemplified by SNP panels comprising variant alleles in one or more of the SNPs designated rs1137100, rs2070874, rs10778534, rs627839, and rs5993891.

12 Claims, 5 Drawing Sheets

A. Seattle Cohort

SNP PANELS FOR PREDICTING PROSTATE CANCER-SPECIFIC MORTALITY

CROSS-REFERENCE TO RELATED APPLICATIONS

The present application claims priority to U.S. Provisional Patent Application No. 61/264,163, filed Nov. 24, 2009, which is incorporated by reference in its entirety.

GOVERNMENT SUPPORT

This invention was made with government support under Grant Nos. RO1 CA 056678, RO1 CA 092579, RO3 CA 121871, RO3 CA 137799, and P50 CA 097186 from the National Cancer Institute, National Institutes of Health. The government has certain rights in the invention.

SEQUENCE LISTING

The present application includes a Sequence Listing in electronic format as a text file entitled "SNP_Seq_Listing_ST25.txt" which was created on Nov. 22, 2010, and which has a size of 7 kilobytes. The contents of txt file "SNP_Seq_Listing_ST25.txt" are incorporated by reference herein.

BACKGROUND OF THE DISCLOSURE

Technical Field of the Disclosure The present disclosure relates, generally, to the fields of genetic epidemiology, cancer biology and oncology. More specifically, provided herein are SNPs and SNP panels for predicting prostate cancer-specific mortality (PCSM) and methods for predicting prostate cancer-specific mortality that employ the presently disclosed SNPs and SNP panels.

DESCRIPTION OF THE RELATED ART

Prostate cancer accounts for over 200,000 cancer diagnoses each year in the United States. Most men at diagnosis have localized tumors that will remain indolent and slow-growing, but at least 20% will progress and some will become fast-growing, aggressive tumors that result in over 30,000 deaths annually in the U.S. Jemal et al., *CA Cancer J. Clin.* 60(5) (2010). Although a number of clinical and pathological features of the disease such as Gleason score, stage and prostate-specific antigen (PSA) level are helpful for making decisions about primary therapy (Partin et al., *JAMA* 277(18): 1445-51 (1997); Ross et al., *J. Urol.* 165(5):1562-8 (2001); Stephenson et al., *J. Natl. Cancer Inst.* 98(10):715-7 (2006)), the inability to accurately stratify individual patients into those with an aggressive versus a more indolent form of the disease leads to under-treatment of patients who may benefit from early, aggressive therapy and over-treatment of many patients whose disease may not have had a significant clinical impact within the lifespan of the patient.

Despite considerable efforts to profile clinically significant prostate cancer based on genetic alterations in tumor tissue, it remains unclear as to the specific molecular changes that correlate with prostate cancer recurrence/progression and mortality. The complexity of the prostate cancer progression process may be explained by genetic polymorphisms that are associated with host susceptibility to a more aggressive prostate cancer phenotype, and which thereby increase the risk for lethal prostate cancer. That is, subtle changes in gene transcription, translation, or the function of gene products due to inherited genetic variants can modify tumor behavior.

Somatic genetic alterations in prostate tumor tissue have been correlated with disease outcomes (Glinsky et al., *J. Clin. Invest.* 113(6):913-23 (2004); Rubin et al., *Cancer Epidemiol Biomarkers Prev.* 14:1424-32 (2005); Mucci et al., *Cancer Epidemiol Biomarkers Prev.* 17(7):1682-8 (2008); Taylor et al., *Cancer Cell* 18(1):11-22 (2010)), but these approaches have technical challenges that may limit their clinical utility. Allison et al., *Nat. Rev. Genet.* 7(1):55-65 (2006); Eisenstein, *Nature* 442(7106):1067-70 (2006); Loannidis, *Oncologist* 12(3):301-11 (2007). In contrast, access to germline DNA and genotyping are straightforward, and genetic background may provide insight on the predisposition for metastatic progression to a lethal outcome. Lindstrom et al., *Lancet Oncol.* 8(11):1001-6 (2007).

Genetic susceptibility is known to play a role in the development of prostate cancer (Lichtenstein et al., *N Engl J Med.* 343(2):78-85 (2000); Thomas et al., *Nat Genet.* 40(3):310-5 (2008); Eeles et al., *Nat Genet.* 40(3):316-21 (2008)) and several sequence variants have been associated with risk of developing more aggressive disease (Duggan et al., *J Natl Cancer Inst.* 99(24):1836-44 (2007); Xu et al., *Proc Natl Acad Sci USA* 107(5):2136-40 (2010)) or biochemical recurrence. Lin et al., *Urologia Internationalis* 83(4):463-70 (2009); Cheng et al., *Cancer Epidemiol Biomarkers Prev.* 19(9):2124-32 (2010); Gallagher et al., *Clin Cancer Res.* 16(10):2819-32 (2010). However, the genetic polymorphisms associated with prostate cancer incidence have not been associated with prostate cancer specific mortality (PCSM). Kote-Jarai et al., *Cancer Epidemiol Biomarkers Prev.* 17(8):2052-61 (2008); Fitzgerald et al., *Clin Cancer Res.* 15(9):3231-37 (2009); Wiklund et al., *Cancer Epidemiol Biomarkers Prev.* 18(5):1659-62 (2009); Penney et al., *Clin Cancer Res.* 15(9):3223-30 (2009); Salinas et al., *Prostate* 69(4):363-72 (2009).

Several SNPs in selected candidate genes (Gallagher et al., *Clin Cancer Res.* 16(10):2819-32 (2010); Hayes et al., *Cancer Epidemiol. Biomarkers Prev.* 15(61:1223-5 (2006); Stark et al., *Cancer Epidemiol. Biomarkers Prev.* 18(6):1859-63 (2009); Holt et al., *Clin. Cancer Res.* 14:3823-31 (2008); Penney et al., *Cancer Prev. Res.* 3(5):604-10 (2010); Holt al., *Prostate* 70(13):1448-60 (2010); Wright et al., *Prostate* 70(10):1094-101 (2010); Nguyen et al., *J. Clin. Oncol.* 28(25):3958-64 (2010)) and two BRCA founder mutations in Ashkenazi Jewish patients (Gallagher et al., *Clin. Cancer Res.* 16(7):2115-21 (2010)) have recently been correlated with PCSM, but results have not been confirmed in independent cohorts. Thus, a connection between inherited genetic variants and case-fatality due to prostate cancer has yet to be established.

Substantial support for the role of cancer modifier loci that may affect tumor development, growth and/or progression derives from studies of animal models. Dragani, *Cancer Res.* 63:3011-8 (2003). Investigations of inbred mice have shown that certain strains harbor genetic variants that clearly influence mammary tumor age of onset and metastatic progression. Lifsted et al., *Int. J. Cancer* 77:640-4 (1998). More recently, Hunter et al. identified Brms1 as a gene with variations that may be responsible for metastatic progression of human breast cancer. *Cancer Res.* 66(3):1251-4 (2006) and Hunter et al., *Cancer Res.* 61:8866-72 (2001).

In relation to prostate cancer, a review by Rebbeck notes that genotypes may alter disease outcomes by: (1) influencing the natural history of the disease by acting directly in tumor etiology or affecting the rate of disease progression or the propensity for metastasis and (2) influencing response to chemoprevention or pharmacological treatment of cancer. Rebbeck, *Cancer Epidemiol. Biom. Prev.* 11:945-952 (2002).

Existing methodology for predicting prostate cancer-specific mortality include determining Gleason score and disease stage in prostate cancer tissue. Genetic markers have not been identified that may be used for predicting a lethal prostate cancer outcome. Prostate cancer is a heterogeneous disease, and standard clinical and pathological features are not reliably accurate for predicting individual patient outcomes. Kattan et al., *J. Natl. Cancer Inst.* 90(10):766-71 (1998) and Andren et al., *J. Urol.* 175(4):1337-40 (2006).

The ability to distinguish patients with aggressive from those with indolent prostate cancer would improve cancer care and facilitate personalized medicine for the 200,000 or more men diagnosed each year. Jemal et al., *CA Cancer J Clin.* 60(5) (2010). Genetic susceptibility is known to play a role in prostate cancer etiology. Thomas et al., *Nat Genet.* 40(3):310-5 (2008); Eeles et al., *Nat Genet.* 40(3):316-21 (2008); Gudmundsson et al., *Nat Genet.* 39(5):631-7 (2007)) and may also mediate its natural history, including the frequency and rate of metastasis that leads to PCSM. Earlier efforts have enumerated a subset of somatic genetic changes correlated with prostate cancer outcomes (Glinsky et al., *J Clin Invest.*113(6):913-23 (2004); Mucci et al., *Cancer Epidemiol Biomarkers Prev.* 17(7):1682-8 (2008); Taylor et al., *Cancer Cell.*18(1):11-22 (2010); and Bismar et al., *Neoplasia* 8(1:59-68 (2006), but the widespread use of these approaches is limited by the availability of appropriately collected and processed tumor tissue samples, heterogeneity in tumor tissue samples (e.g., multifocal disease), and the lack of reproducible and validated results. Allison et al., *Nat Rev Genet.* 7(1):55-65 (2006); Eisenstein, *Nature* 442(7106):1067-70 (2006); Loannidis, *Oncologist* 12(3):301-11 (2007); Lin et al., *J. Clin. Oncol.* 24(23):3763-70 (2006). By comparison, genotyping of sequence variants using DNA extracted from a whole blood or saliva sample, both of which can be easily obtained in the clinic, can be accomplished at low cost and provide accurate, reproducible results which could be used for stratification of patients at diagnosis into those at higher risk for dying from prostate cancer.

What is critically needed in the art are gene-based diagnostic and prognostic assays that permit the stratification of patient risk, disease progression and mortality that characterize an individual patient who will die of his prostate cancer.

SUMMARY OF THE INVENTION

The present disclosure addresses these and other related needs, and advances knowledge of the genetic epidemiology and molecular genetics of aggressive prostate cancer by providing, inter alia, SNP panels and methods for predicting prostate cancer-specific mortality that employ the presently disclosed SNP panels.

One embodiment of the present disclosure provides SNP panels for predicting prostate cancer-specific mortality in a human patient wherein the panels comprise variant alleles in one, two, three, four, five, or more of the SNPs designated rs1137100, rs228697, rs2839685, rs1799814, rs627839, rs5993891, rs635261, rs11710277, rs11205, rs2494750, rs4608577, rs4645959, rs1799964, rs25487, rs2308327, rs915927, rs2070874, rs1029153, rs12467911, rs10778534, rs523349, and rs4583514. Within certain aspects of these embodiments, the present disclosure provides SNP panels for predicting prostate cancer-specific mortality in a human patient wherein the panel comprises variant alleles in one, two, three, four, or five of the SNPs designated rs1137100, rs2070874, rs10778534, rs627839, and rs5993891.

Another embodiment of the present disclosure provides methods for predicting prostate cancer-specific mortality in a human patient wherein the methods comprise the step of detecting variant alleles in one, two, three, four, five, or more of the SNPs designated rs1137100, rs228697, rs2839685, rs1799814, rs627839, rs5993891, rs635261, rs11710277, rs11205, rs2494750, rs4608577, rs4645959, rs1799964, rs25487, rs2308327, rs915927, rs2070874, rs1029153, rs12467911, rs10778534, rs523349, and rs4583514. Within certain aspects of these embodiments, the present disclosure provides methods for predicting prostate cancer-specific mortality in a human patient wherein the methods comprise the step of detecting variant alleles in one, two, three, four, or five of the SNPs designated rs1137100, rs2070874, rs10778534, rs627839, and rs5993891.

These and other aspects of the present disclosure will become apparent upon reference to the following detailed description and attached drawings. All publications, patents, and patent applications cited herein, whether supra or infra, are hereby incorporated by reference in their entirety.

DETAILED DESCRIPTION OF THE DISCLOSURE

Figure 1:
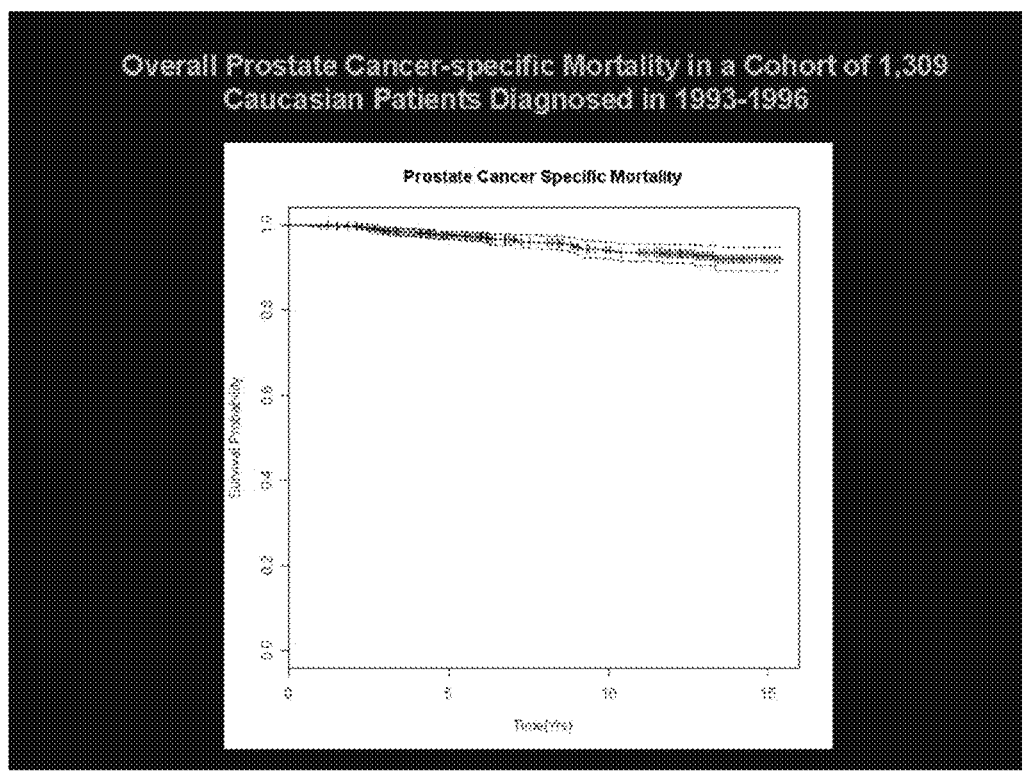
FIG. 1 is a graph depicting the overall prostate cancer-specific mortality in a cohort of 1,309 Caucasian patients diagnosed in either 1993-1996 or in 2002-2005.

As indicated above, the present disclosure is based upon the observation that certain SNPs are associated with prostate cancer-specific mortality (PCSM) and that these individual SNPs, and panels thereof, may be advantageously employed for the prediction of prostate cancer-specific mortality in patients.

As used herein, the term "single nucleotide polymorphism" (SNP) refers to a DNA sequence variation occurring when a single nucleotide—A, T, C, or G—in the genome differs between members of a species (or between paired chromosomes in an individual). For example, two DNA fragments from different individuals having the sequences AAGC<u>C</u>TA and AAGC<u>T</u>TA contain a difference in a single nucleotide, which create two alleles C and T. Within a population, SNPs can be assigned a minor allele frequency (MAF)—the lowest allele frequency at a locus that is observed in a particular population. This is simply the lesser of the allele frequencies for single-nucleotide polymorphisms, which may be referred to as the less common allele.

Quite surprisingly, it was discovered as part of the present disclosure that allelic variation plays a role in metastatic efficiency of prostate cancer—that is, the success or failure of a prostate tumor to spread or recur and to lead to patient death. The underlying genetic predisposition to a more aggressive form of prostate cancer was examined in association with mortality in DNA samples from a population-based cohort of incident prostate cancer patients. DNA from such patients was employed in genetic studies and patient outcome was measured by, for example, disease recurrence, progression, and/or PC-specific mortality.

To search for genetic markers that may distinguish high-risk patients for PCSM, SNPs were genotyped in or near 156 candidate genes in biological pathways of interest for prostate cancer progression (e.g., androgens, inflammation, DNA damage, growth factors) as well as in recently identified risk-associated loci from GWAS (Thomas et al., *Nat. Genet.* 40(3): 310-5 (2008) and Eeles et al., *Nat. Genet.* 40(3):316-21 (2008)) in a population-based cohort of prostate cancer patients. 937 single nucleotide polymorphisms (SNPs) were genotyped in genes from biological pathways of interest as well as risk-associated SNPs in a population-based cohort of 1,309 prostate cancer patients of European ancestry. Permutation testing was used to select SNPs (p≤0.01) associated with prostate cancer-specific mortality (PCSM), which were then validated in an independent cohort of 2,875 prostate cancer patients.

The top ranked sequence variants associated with fatal disease were then genotyped in an independent cohort of prostate cancer patients for validation. The results reported herein identify a panel of five SNP genotypes that are associated with fatal prostate cancer outcomes. Variants in several candidate genes have previously been associated with PCSM. Those variants include MIC-1 (Hayes et al., *Cancer Epidemiol. Biomarkers Prev.* 15(6):1223-5 (2006)); September 15 (Penney et al., *Cancer Prev. Res.* 3(5):604-10 (2010)); VDR, CYP27B1, and CYP24A1 (Holt et al., *Prostate* 70(13):1448-60 (2010)); TLR-9 (Stark et al., *Cancer Epidemiol. Biomarkers Prev.* 18(6):1859-63 (2009)); Megalin (Holt et al., *Clin Cancer Res.* 14:3823-31 (2008)); CYP17 (Wright et al., *Prostate* 70(10):1094-101 (2010)); and FASN (Nguyen et al., *J. Clin. Oncol.* 28(25):3958-64 (2010)). In addition, two founder mutations in BRCA1 and BRCA2 as well as SNPs in two risk-associated loci (19q13 and 11q13) were shown to increase risk for PCSM in Ashkenazi Jewish patients. Gallagher et al., *Clin. Cancer Res.* 16(10):2819-32 (2010) and Gallagher et al., *Clin. Cancer Res.* 16(7):2115-21 (2010). None of these earlier results, however, have been validated in independent cohorts and thus these findings may represent false-positives. In the present disclosure, some of these same variants were interrogated, but none was among the top ranked SNPs in our analysis that simultaneously considered 847 variants.

Five of the 22 highest ranking SNPs (see, Table 1) were validated (p≤0.05) as being associated with PCSM. After adjusting for age and clinicopathological factors, the strongest evidence was for rs1137100, a non-synonymous SNP in the LEPR gene (hazard ratio, HR=0.82, 95% CI 0.67-1.00, p=0.05). Four other SNPs, one each in the RNASEL, CRY1, IL4, and ARVCF genes, were also validated. Compared to patients with 0-2 at-risk genotypes those with 4-5 at-risk genotypes had a 50% (95% CI 1.2-1.9) higher risk of PCSM in multivariate analyses, and risk increased with number of at-risk genotypes (p-trend=0.001).

TABLE 1

Sequences of the 22 Highest Ranking SNPs

| SNP Identifier | Sequence Identifier | Nucleotide Sequence (5'-3') |
|---|---|---|
| rs1137100 | SEQ ID NO: 1 | CTTATGTGCAGACAACATTGAAGGAA[A/G]GACATTTGTTTCAACAGTAAATTCT |
| rs228697 | SEQ ID NO: 2 | TTATGACCGTTTTCCTGCCTGACCCC[C/G]CTGTCTGTCCTCTGTTGTCGCCATC |
| rs2839685 | SEQ ID NO: 3 | AAAGGGGCGCTCTCCTCACCCCCACG[C/T]CTCCTGGGTGCCGACCTGCACCCTC |
| rs1799814 | SEQ ID NO: 4 | GGGCAAGCGGAAGTGTATCGGTGAGA[A/C]CATTGCCCGCTGGGAGGTCTTTCTC |
| rs627839 | SEQ ID NO: 5 | CCCAGGGTCTCCTCCAGAGGAAGGTT[G/T]TGCTGTTCTTTACCCAAATCATCTT |
| rs5993891 | SEQ ID NO: 6 | AATCCCTCTCTAGCTGCCCTGTACCT[C/T]ACCCTCTAAGCACCCCTAAACCAAA |
| rs635261 | SEQ ID NO: 7 | TGTCCCAAATGAAACTCTTGGTCTTC[C/G]CTCTAAACCTGCTCCTCTGGAAGCC |
| rs11710277 | SEQ ID NO: 8 | TGGGCACCCCAGCCAGGTCTAGAGCC[A/G]GAAGGGTGTGAGGGTCAAGCAGCCC |
| rs11205 | SEQ ID NO: 9 | ATAATGATGTGTCAAGATTCAAGGCA[A/G]TTAAGGTAAATGTGTATTACTACGT |
| rs2494750 | SEQ ID NO: 10 | CCCCTTTCTCCTGGACACTCACAGGA[C/G]AGTGCAGGTGACTGCCACCCCGACC |
| rs4608577 | SEQ ID NO: 11 | ACCTTATAAATCTCCACTACCATGTT[G/T]TTGCTTGGACTGTTCACACTTCCTG |
| rs4645959 | SEQ ID NO: 12 | CCTCAACGTTAGCTTCACCAACAGGA[A/G]CTATGACCTCGACTACGACTCGGTG |
| rs1799964 | SEQ ID NO: 13 | GGGAAGCAAAGGAGAAGCTGAGAAGA[C/T]GAAGGAAAAGTCAGGGTCTGGAGGG |
| rs25487 | SEQ ID NO: 14 | CCGCATGCGTCGGCGGCTGCCCTCCC[A/G]GAGGTAAGGCCTCACACGCCAACCC |
| rs2308327 | SEQ ID NO: 15 | GGCCCATGAAGGCCACCGGTTGGGGA[A/G]GCCAGGCTTGGGAGGGAGCTCAGGT |
| rs915927 | SEQ ID NO: 16 | CCCTTCATAGTCACAGCCAGCGACCC[A/G]GCAGGACCTAGCTATGCAGCTGCTA |
| rs2070874 | SEQ ID NO: 17 | GTTAGCTTCTCCTGATAAACTAATTG[C/T]CTCACATTGTCACTTGCAAATCGACA |
| rs1029153 | SEQ ID NO: 18 | AGGAAGTAGGAAGTAAATTATAGTGA[C/T]GTAATCTTGAATTGTAACTGTTCTT |
| rs12467911 | SEQ ID NO: 19 | GTCTGGATATCTGTGACCTAGAAATC[C/T]GGAGTACAGCACCCTGGGGGCTCTT |
| rs10778534 | SEQ ID NO: 20 | ACATGGACATGGGAGTCCTGCAATTA[C/T]AAGACTCCAAGAAGGCCATATGACT |
| rs523349 | SEQ ID NO: 21 | AAAACGCTACCTGTGGAAGTAATGTA[C/G]GCAGAAGAGGCCCAGAAGTACCGTC |
| rs4583514 | SEQ ID NO: 22 | GTATTGTCTTAAAAGAGTGATTGATG[A/G]TAGCTACGGAAAACTTTGATTTTTA |

The panel of 22 SNPs was tested in an independent cohort of prostate cancer patients, all of European ancestry. SNP rs1137100 in the LEPR gene was validated to be the strongest marker associated with PCSM. In addition, another four variants, rs2070874 (p=0.02), rs10778534 (p=0.04), rs5993891 (p=0.048), and rs627839 (p=0.05) showed evidence of validation when adjusting for different covariates than those included in the original Seattle model. Inheritance of all five at-risk variants was associated with a 50% to 70% higher risk for fatal outcomes, and PCSM increased according to number of at-risk genotypes (p-trend=0.0005 adjusting for age alone; p-trend=0.001 adjusting for age plus clinicopathological factors). Within both cohorts, there was a similar prevalence of carriers of four (28%) or five (6%) at-risk genotypes.

The minor allele of SNP rs1137100 encodes a non-synonymous variant in exon 4 of the leptin receptor (LEPR) gene. LEPR is a cytokine receptor that binds and transduces the signaling cascade of leptin, a paracrine and autocrine hormone. Downstream effects of this protein-receptor interaction include stimulation of pubertal prostate growth (Mantzoros et al., *J. Clin. Endocrinol. Metab.* 82(41:1066-70 (1997)); inflammation (Loffreda et al., *FASEB J.* 12(11:57-65 (1998)); angiogenesis (Sierra-Honigmann et al., *Science* 281 (5383):1683-6 (1998)); and bone mass regulation (Duey et al., *Cell* 100(2):197-207 (2000)), which make LEPR an interesting candidate for tumor progression. Ribeiro et al., *Eur. J. Cancer Prev.* 13(5):359-68 (2004). Notably, the primary metastatic site for prostate cancer is the bone and this event is associated with a high probability of PCSM. Norgaard et al., *J. Urol.* 184(1):162-7 (2010); Hsiao et al., *J. Urol.* 184(2):512-8 (2010); Rana et al., *Br. J. Urol.* 72(6):933-6 (1993).

An additional four SNPs were confirmed to be associated with PCSM. Variant rs627839 tags the RNASEL gene, a candidate gene for the hereditary prostate cancer 1 (HPC1) locus. Carpten et al., *Nat. Genet.* 30:181-4 (2002). A role in prostate cancer has been suggested through the protein's ability to increase apoptosis and inhibit inflammation, prostate cancer cell proliferation and adhesion. Malathi et al., *Proc. Natl. Acad. Sci. USA* 102(41):14533-8 (2005) and Xiang et al., *Cancer Res.* 63(20):6795-801 (2003). Thus, a loss of function has mechanistic rationale for an association with aggressive prostate cancer. Of the five genes highlighted herein, this is the only one previously evaluated in relation to PCSM. In an analysis of RNASEL tagSNPs, including rs627839, Meyer and colleagues found no associations with prostate cancer mortality. *Carcinogenesis* 31(9):1597-603 (2010).

Variant rs2070874 is in the promoter region of Interleukin 4 (IL4), which plays a role in carcinogenesis via activation of the Stat6 transcription factor. Witthuhn et al., *Nature* 370 (6485):153-7 (1994). Studies have shown that IL4 directly inhibits tumor cell growth (Toi et al., *Cancer Res.* 52(21: 275-9 (1992); Obiri et al., *J. Clin. Invest.* 91(1):88-93 (1993); Topp et al., *Blood* 82(9):2837-44 (1993); Lahm et al., *Int. J. Cancer* 59(3):440-7 (1994)); prevents invasion and migration of colon cancer cells (Uchiyama et al., *J. Cell Biochem.* 62(4):443-53 (1996)); and is a potent inhibitor of angiogenesis. Volpert et al., *J. Exp. Med.* 188(6):1039-46 (1998). Of interest, rs2070874 is in perfect LD with rs2243250, a promoter variant for which the minor allele confers diminished IL4 expression. Rosenwasser et al., *Am. J. Respir. Crit. Care Med.* 156(4 Pt 2):S152-5 (1997). Therefore, carriers of the rs2070874 minor allele associated with PCSM in this study are also likely to have reduced IL4 expression.

SNP rs10778354 tags the Cryptochrome 1 (CRY1) gene, which is involved in the regulation of circadian rhythm. Young et al., *Nat. Rev. Genet.* 2(9):702-15 (2001); Reppert et al., *Nature* 418(6901):935-41 (2002); Kondratov et al., *Cell Cycle* 5(8):890-5 (2006). Androgen production in healthy young men displays circadian variation (Plymate et al., *J. AndroL* 10(5):366-71 (1989); Guignard et al., *Acta Endocrinol.* 94(4):536-45 (1980)) and disruption of the circadian rhythm through jetlag or rotating shift work has been shown to increase the risk of several cancers, including prostate. Band et al., *Am. J. Epidemiol.* 143(2):137-43 (1996) and Irvine et al., *Aviat. Space Environ. Med.* 70(6):548-55 (1999). It has recently been shown that several circadian gene polymorphisms are associated with prostate cancer risk, but no association was observed for rs10778534. Zhu et al., *Cancer Res.* 69(24):9315-22 (2009). This may suggest that rs10778534 or a functional SNP in linkage disequilibrium with it plays a role later in the disease process.

Finally, rs5993891 is located in intron 17 of the ARVCF gene, a member of the p120catenin family of proteins implicated in regulation of transcriptional activity, regulation of Rho GTPases and modulation of cadherin-mediated adhesion. Increased expression of ARVCF has been shown to disrupt cell adhesion, potentially through the regulation of the GTPase Rac. Reintsch et al., *Dev. Dyn.* 237(9):2328-41 (2008). This SNP also tags the COMT gene, positioned immediately centromeric to ARVCF. COMT works to neutralize the genotoxic effects of the catechol estrogens to yield an anti-proliferative and anti-angiogenic metabolite (Guldberg et al., *Pharmacol. Rev.* 27(2):135-206 (1975)); Fotsis et al., *Nature* 368(6468):237-9 (1994)); and the soluble isoform is down-regulated in the highly metastatic LNCaP-LN3 prostate cancer cell line. Glen et al., *J. Proteome Res.* 7(3):897-907 (2008).

The five sequence variants highlighted herein represent the first such evidence for this panel of genetic markers to be associated with PCSM. Of note, two genetic variants (rs228697 in PER3 and rs1029153 in CXCL12) identified as potential predictors of PSCM in the Seattle cohort were not evaluated in the Swedish cohort due to genotyping failure. Thus, additional investigation of these variants is warranted. The strengths of this approach include the focus on population-based patient cohorts, the discovery-validation study design, the large number of patients and outcomes in the validation cohort, and the focus on a large number of genetic variants in or tags for genes in biological pathways of interest for disease progression. One potential concern is the difference in clinicopathological factors and treatment approaches between the two cohorts. To accommodate these dissimilar features, adjustment covariates were allowed to vary in the Cox models. Further, the focus on fatal events reduced potential bias related to different screening practices between the two cohorts that likely contribute to their different distributions of clinicopathological characteristics. Interestingly, the proportion of all patients carrying 4-5 of the at-risk genotypes was identical in the Seattle and Swedish cohorts (i.e., 34%). Because Gleason score and stage are strong predictors of PSCM, adjustment for these factors in the multivariate models may diminish the magnitude of SNP-PCSM associations. Thus, in addition to presenting results adjusted for clinicopathological factors, results are also adjusted for age alone. Although the presently disclosed 5-SNP panel was validated in an independent cohort of European descent, it would be of interest to evaluate the full panel of 22 SNPs in other U.S. patient cohorts as well as African American patients who are at higher risk for fatal prostate cancer.

It is demonstrated herein that a SNP (rs1137100) in LEPR is associated with lethal prostate cancer and that an additional four variants that increase the risk of PCSM. Three of these genetic polymorphisms (rs1137100, rs2070874, rs10778534) were significantly associated with fatal prostate cancer in multivariate models that included the traditional factors (i.e., Gleason score, stage) used to predict outcomes, suggesting that these genetic variants contribute independent data beyond the standard variables used to predict prognosis. Two other SNPs (rs627839, rs5993891) were validated to be associated with PCSM in models that adjusted for age alone. This panel of five SNPs was significantly associated with PCSM, and there was evidence for a dose-response effect according to the number of at-risk genotypes a patient carried. The data presented herein suggest the clinical utility of this 5-SNP panel for stratification of patients at the time of diagnosis into those at higher risk for adverse outcomes. Understanding the individual prostate cancer patient's risk for progression to a lethal phenotype facilitates informed counseling of patients regarding therapy options, follow-up plans and approaches for secondary prevention. These data further suggest that such high-risk patients will benefit most from early aggressive therapy and that these patients are ideal candidates for novel adjuvant treatment trials aimed at improving patient survival.

Predicting Prostate Cancer Mortality by Combining SNPs with Clinical Variables

A population-based patient cohort, such as described in Example 1, infra, may be employed to permit: (1) the evaluation of SNP-disease outcomes (hazard ratios); (2) the classification of prostate cancer prognoses (e.g., sensitivity, specificity, and receiver operating characteristic (ROC) curve for prostate cancer-specific death within a defined time period following diagnosis); and (3) calculation of absolute probabilities (risks) of dying during the follow-up period (e.g., positive predictive value (PPV) and negative predictive value (NPV) for prostate cancer-specific death within a defined time-period after diagnosis) among men with various genotypes, clinical, tumor, and patient characteristics.

Data from a prostate cancer patient cohort may be used to rank and prioritize SNPs and the validation cohorts may be used to confirm the individual and combined SNPs and refine the prediction models from the prostate cancer patient cohort. For example, the process may comprise the following steps: (1) selection of SNPs; (2) validation of SNPs and functional groups (e.g., androgen pathway) of SNPs; (3) construction of a classifier; and (4) construction of a nomogram.

SNP Selection

Using prostate cancer patient cohort data, SNP and prostate cancer-mortality associations may be examined using Cox regression and weighted logistic regression (WLR). The WLR procedure focuses on optimizing discriminating power over time, allowing time-specific risk scores under a flexible time-varying logistic regression model (i.e., it does not require the constant hazard ratio assumption of Cox regression), and maximizing the time-specific ROC curves when the model assumption holds.

Censoring of the WLR may be incorporated by using the inverse selection probability as a weight. The ROC curve for 10-year prostate cancer-specific mortality may be based on this procedure. WLR may be used as the primary model building tool. Cox regression may be used in parallel to model event time with censoring. Cox models are typically used to generate hazard ratios and associated 95% confidence intervals for each SNP genotype, under a range of genetic models as described in the Examples, infra.

Each candidate SNP genotyped in a prostate cancer patient cohort may be examined by adding it to the WLR model with other known pertinent clinical variables for prognosis (e.g., Gleason score, diagnostic PSA, stage, primary therapy, and age at diagnosis). A two-degree of freedom likelihood ratio test may be used for the effect of three genotypes under a log-additive genetic model (coding the common homozygote as the reference group) in WLR (or Cox regression). A SNP is selected if this test is significant at alpha=0.15. By employing a validation study, the choice of alpha=0.15 enhances the selection of predictive SNPs, with most of the false-positive findings caught in the second stage.

A log-additive model (i.e., a linear dose-response relationship from homozygote wild-type to homozygote variant) may be used to capture possible genetic effects as well as to consider other genetic models (e.g., recessive, dominant). All SNPs significant at the alpha=0.15 level may be examined further for the mode of genetic effects (e.g., recessive, dominant, log-additive). The inclusion of other clinical factors in the model may be employed to select SNPs that have the best chance of being complementary to clinical variables currently used to predict prognosis.

After completion of models adjusting for age only and for age plus clinical factors, under the three possible genetic models (recessive, dominant, log-additive), permuted p-values and associated false-discovery rates may be computed and used for ranking SNP results. From these analyses, a group of SNPs with p-values ≤0.01 and false-discovery rates of ≤0.70 may be identified that constitutes a panel of SNPs to be used for validation.

Validating Selected SNPs in Other Cohorts

The selected SNPs may be validated through genotyping in other independent cohorts of prostate cancer patients. To confirm a SNP's prostate cancer-mortality association in another cohort, a one-sided alpha=0.05 may be used in testing its regression coefficient. To confirm its clinical potential, the risk scores computed from the models built from the cohort data may be used to plot time dependent ROC curves for prostate cancer-specific mortality at 5-year and 10-year intervals after diagnosis. These ROC curves may be compared to those from a prostate cancer patient cohort. Typically, regress toward the ROC curve is expected based on clinical variables alone because of the "optimism" when one predicts data using the model built from a similar dataset. A SNP or group of SNPs for which the AUC is significantly larger than that of clinical variables alone on the validation dataset(s) may be considered as validated. This two-stage (discovery then confirmation) approach largely eliminates the false-positive findings due to multiple testing.

Constructing a Classifier

Data from a prostate cancer patient cohort may be used to refine the models, based on the validated SNPs and clinical variables. SNPs that are not validated in the independent cohort(s) are not used. Combining data from various cohorts allows more accurate estimates of parameters and thereby refines the models. The risk scores from the refined models are treated as a composite "marker" to produce ROC curves at different years after diagnosis. The AUC is compared to the model based on clinical variables alone.

Constructing a Nomogram

While ROC curves summarize a markers' classification performance, the ultimate goal is to help patients make appropriate treatment choices. To develop an absolute risk prediction model and nomogram, WLR or Cox regression may be applied using the inverse of sampling probability as a weight. This weight can be multiplied by the weight for handling censoring in WLR. This type of weighted Cox regression analysis has been widely used in case-cohort studies as a preferred approach. The inverse weighting of the sampling probability makes the analysis mimic a cohort in which all prostate cancer patients ascertained by a cancer registry, such as the Seattle-Puget Sound SEER registry, may be evaluated. The sampling probability for each patient is readily available by design. Thus, the predicted probability of dying of prostate cancer at a specific year after diagnosis from WLR represents the absolute risk of prostate cancer-mortality. The construction of a nomogram from Cox regression is similar to that of Kattan (Kattan et al., *J. Natl. Cancer Inst.* 90(10):766-71 (1998)), except that SNP predictors and clinical data for a population-based cohort are available. In contrast, Kaftan's cohort includes patients from two surgeons.

The nomogram constructed may be further validated by using data from a PLCO (Prostate, Lung, Colon and Ovary Cancer) screening study. Data from a genome-wide SNP association study (CGEMS) for prostate cancer patients and controls ascertained from the PLCO study is publicly available. A prediction model and nomogram may have some "optimism" (i.e., over-estimation of performance) because the final model typically uses the original prostate cancer patient cohort data from which an initial SNP selection is based. An unbiased estimator of "optimism" may be generated by determining the difference in performance between the original prostate cancer patient cohort and external validation using the PLCO data.

The analyses of the secondary outcome, disease recurrence/progression, are similar to those for the primary outcome. Similarly, the classifier and nomogram for recurrence/progression may be constructed. If the classifiers and nomograms do not have adequate performance for clinical use (this could happen, for example, if the informative SNPs, though statistically associated with prostate cancer-specific mortality, are not strong enough to significantly improve the ROC curve), these informative individual SNPs still find utility as building blocks for future classifiers or nomograms when more prognostic markers become available.

Assessing SNPs Without Clinical Variables in a Model

The primary goal of the present disclosure is to improve a prognosis prediction model by incorporating SNP information with clinical variables. The secondary goal is to identify SNPs for their prognosis potential alone so those predictive SNPs can be compared with the SNPs identified that are associated with prostate cancer aggressiveness. These two sets of SNPs may have substantial overlap, which confirms that these SNPs are associated with both prostate cancer aggressiveness and mortality. SNPs strongly associated with prognosis alone may not form the same set of SNPs that are complementary to clinical variables because they could simply explain the underlying genetics that dictate clinical phenotypes such as Gleason score.

To address the multiple comparison concern stemming from a single stage analysis, a permutation distribution of the parameter estimates under the null hypothesis may be generated by scrambling the prostate cancer-specific mortality indicators among subjects and deriving the empirical p-values to control experiment-wise type-I error. This approach is more powerful than Bonferroni adjustment because it takes into account the dependencies among SNPs in adjusting p-values, while Bonferroni assumes that all tests are independent.

Methods for Predicting Prostate Cancer Mortality in a Human Patient

As summarized above, the present disclosure provides, within certain embodiments, methods for predicting prostate cancer mortality in a human patient. These methods comprise the step of detecting variant alleles in one, two, three, four, five, or more of the following SNPs: rs1137100, rs228697, rs2839685, rs1799814, rs627839, rs5993891, rs635261, rs11710277, rs11205, rs2494750, rs4608577, rs4645959, rs1799964, rs25487, rs2308327, rs915927, rs2070874, rs1029153, rs12467911, rs10778534, rs523349, and rs4583514. Within certain aspects, these methods comprise the step of detecting variant alleles in one, two, three, four, or five of the following SNPs: rs1137100, rs2070874, rs10778534, rs627839, and rs5993891.

Determination of the presence or absence of a particular variant allele in a SNP is generally performed by analyzing a nucleic acid sample that is obtained from a human patient. A nucleic acid may be isolated from a human sample by using a method known to those skilled in the art. For example, DNA or RNA can be directly purified from white blood cells or other tissues and SNPs may be detected using oligonucleotide primers and/or probes by hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the PPIB mutations described herein.

A hybridization probe is an oligonucleotide capable of binding specifically to a complementary strand of a nucleic acid. When used to detect a polymorphic site within a nucleic acid, a probe is capable of hybridizing with a nucleic acid derived from one human sample (e.g., a nucleic acid that does not contain a SNP of interest) but does not hybridize under the same conditions with a nucleic acid derived from a second human sample (e.g., a nucleic acid containing a SNP of interest). Typically, a probe is designed such that its central site is the polymorphic site of the SNP, for example the $7^{th}$ position in a probe consisting of 15 nucleotides, or the $8^{th}$ or $9^{th}$ position in a probe consisting of 16 nucleotides. In this way, a hybridization difference for different alleles can be obtained. According to an embodiment of the present disclosure, the probe can be used in a diagnosis method for predicting PCSM. The diagnosis method may be Southern blotting in which detection is performed using the hybridization of nucleic acids of a method in which a microarray to which the probe was bound in advance is used.

A microarray for predicting PCSM according to another aspect of the present disclosure includes a polynucleotide or the complement thereof, the polynucleotide hybridized with one of the polynucleotides, a polypeptide encoded by one of the polynucleotides or cDNA thereof according to an embodiment of the present invention. A microarray may be prepared using a conventional method known to those skilled in the art using the polynucleotide or the complementary polynucleotide thereof, the polynucleotide hybridized with the probe, the polypeptide encoded by one of the polynucleotides or cDNA thereof according to an embodiment of the present invention. For example, the polynucleotide may be fixed to a substrate coated with an active group of amino-silane, poly-L-lysine and aldehyde. The substrate may be composed of a silicon wafer, glass, quartz, metal, or plastic. The method of fixing the polynucleotide to the substrate may be either micropipetting using piezoelectric or a method using a pin-shaped spotter.

Hybridization should be done in order to distinguish the bases of a SNP at the polymorphic sites specifically. A hybridization reaction is typically performed under stringent conditions such as, for example, in a salt concentration of 1 M or less and at a temperature of 25° C. or higher. For example, 5×SSPE (750 mM NaCl, 50 mM Na Phosphate, 5 mM EDTA, pH 7.4) and 25° C. to 30° C. may be suitable conditions for the allele specific probe hybridization. The hybridization conditions may be changed according to desired use by those skilled in the art.

Amplification of a nucleic acid from a human patient may be carried out by one of polymerase chain reaction (PCR), ligase chain reaction (LCR) (Wu and Wallace, *Genomics* 4, 560(1989), Landegren etc., *Science* 241, 1077(1988)), transcription amplification (Kwoh etc., *Proc. Natl. Acad. Sci. USA* 86, 1173(1989)), self-sustained sequence replication (Guatelli etc., *Proc. Natl. Acad. Sci. USA* 87, 1874(1990)) and Nucleic Acid Sequence Based Amplification (NASBA).

The polymerase chain reaction (PCR) can be employed to amplify a target nucleic acid comprising one of the SNPs disclosed herein. Briefly, a target nucleic acid, for example DNA or RNA from a human patient, can be combined with sense and antisense primers, dNTPs, DNA polymerase, and other reaction components. The sense primer can anneal to the antisense strand of a nucleic acid sequence of interest. The antisense primer can anneal to the sense strand of the nucleic acid at a location downstream to the sense primer and the SNP to be amplified and/or detected. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

Although the methods typically employ PCR steps, other amplification protocols may also be used. Suitable amplification methods include ligase chain reaction (see, e.g., Wu and Wallace, *Genomics* 4:560-569, 1988); strand displacement assay (see, e.g., Walker et al., *Proc. Natl. Acad. Sci. USA* 89:392-396 (1992); U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177 (1989); and self-sustained sequence replication (3SR) (Guatelli et al., *Proc. Natl. Acad. Sci. USA* 87:1874-1878 (1990); WO 92/08800). Alternatively, methods that amplify the probe to detectable levels can be used, such as Q($\beta$-replicase amplification (Kramer and Lizardi, *Nature* 339:401-402 (1989); Lomeli et al., *Clin. Chem.* 35:1826-1831 (1989). A review of known amplification methods is provided, for example, by Abramson and Myers in *Current Opinion in Biotechnology* 4:41-47 (1993).

Amplified products can be detected using any means known in the art, including, e.g., restriction fragment length polymorphism (RFLP) analysis; denaturing gel electrophoresis (see, e.g., Erlich, PCR Technology, Principles and Applications for DNA Amplification (W. H. Freeman and Co, New York, 1992, Chapter 7), direct sequencing, and HPLC-based analysis. Suitable sequence methods include, e.g., dideoxy sequencing-based methods and Maxam and Gilbert sequence (see, e.g., Sambrook and Russell, *Molecular Cloning, A Laboratory Manual* (3rd Ed, 2001)). Suitable HPLC-based analyses include, e.g., denaturing HPLC (dHPLC) as described in e.g., Premstaller and Oefner, *LC-GC Europe* 1-9 (July 2002); Bennet et al., *BMC Genetics* 2:17 (2001); Schrimi et al., *Biotechniques* 28(4):740 (2000); and Nairz et al., *PNAS USA* 99(16):10575-10580 (2002); and ion-pair reversed phase HPLC-electrospray ionization mass spectrometry (ICEMS) as described in e.g., Oberacher et al.; *Hum. Mutat.* 21(1):86 (2003). Other methods for characterizing single base changes in PPIB alleles include, e.g., single base extensions (see, e.g., Kobayashi et al., *Mol. Cell. Probes* 9:175-182 (1995); single-strand conformation polymorphism analysis, as described, e.g., in Orita et al., *Proc. Nat. Acad. Sci. USA* 86:2766-2770 (1989), allele specific oligonucleotide hybridization (ASO) (e.g., Stoneking et al., *Am. J. Hum. Genet.* 48:70-382 (1991); Saiki et al., *Nature* 324:163-166 (1986); and sequence-specific amplification or primer extension methods as described in, for example, WO93/22456 and U.S. Pat. Nos. 5,137,806; 5,595,890; 5,639,611; and 4,851,331; 5'-nuclease assays, as described in U.S. Pat. Nos. 5,210,015; 5,487,972; and 5,804,375; and Holland et al., *Proc. Natl. Acad. Sci. USA* 88:7276-7280 (1988).

Sequencing the isolated DNA may be performed through various methods known to those skilled in the art. For example, the nucleotides of nucleic acids may be directly sequenced using a dideoxy method. Also, the nucleotides of the polymorphic sites may be sequenced by hybridizing the DNA with a probe containing the sequence of the SNP site or a complementary probe thereof, and examining the degree of the hybridization. The degree of hybridization may be measured using a method of indicating a detectable index of the target DNA and specifically detecting the hybridized target, or using an electrical signal detecting method. The determining of the genotype of a polymorphic site may include hybridizing the nucleic acid sample isolated from the subject with the polynucleotide including the SNP according to an embodiment of the present invention and a polynucleotide hybridized with the polynucleotide, and detecting the results of the hybridization. Additionally, determining the genotype of a SNP may be performed using the mass spectrometry method of the Examples, or any other suitable methods known in the art.

Oligonucleotide primers and/or probes can be prepared by any suitable method, including chemical synthesis using commercially available reagents and instruments. Alternatively, oligonucleotides can be purchased through commercial sources. Methods for synthesizing oligonucleotides are well known in the art, for example, by reference to Narang et al., *Meth. Enzymol.* 68:90-99 (1979); Brown et al., *Meth. Enzymol.* 68:109-151 (1979); and Beaucage et al., *Tetrahedron Lett.* 22:1859-1862 (1981). The length of the primers may vary according to the purpose of use, but are usually 15 to 30 nucleotides. A short primer molecule generally requires a lower temperature to be stably hybridized with the template. The primer sequence does not necessarily need to be completely complementary to the template, but should be sufficiently complementary to be hybridized with the template.

Detection techniques for evaluating nucleic acids for the presence of a SNP involve procedures well known in the field of molecular genetics. Further, many of the methods involve amplification of nucleic acids. Ample guidance for performing the methods is provided in the art. Exemplary references include manuals such as PCR Protocols: A Guide to Methods and Applications (eds. Innis, et al., Academic Press, San Diego, Calif., 1990); Ausubel, Current Protocols in Molecular Biology (1994-1999), including supplemental updates through April 2004; Sambrook and Russell, *Molecular Cloning, A Laboratory Manual* (3rd Ed, 2001).

SNPs may also be detected using restriction fragment length polymorphism (RFLP) analysis. For example, sequences comprising one or more of the SNPs described herein can be amplified using primers comprising sequences flanking the SNP. Where the SNP results in the addition or deletion of a restriction endonuclease recognition sequence, that restriction endonuclease can be employed to detect the presence or absence of the SNP in the amplified nucleic acid. Following digestion, the restriction fragments can be analyzed using any methods known in the art including, for example, gel electrophoresis.

The SNP panels disclosed herein are useful tools for more specific and sensitive diagnosis of prostate cancer and/or the prognosis of PCSM. For example, nucleic acids that specifically hybridize to a nucleic acid comprising one or more of the presently disclosed SNPs can be used to identify human patients susceptible to the development of or afflicted with. The method of diagnosing prostate cancer and/or prognosing PCSM in a human patient typically includes assessing whether the patient belongs to a high risk group having a high incidence or probability of prostate cancer when the genotype for one or more SNP matches the genotype associated with prostate cancer as disclosed herein. Additionally, the method may comprise determining the genotype of each SNP in the selected panel of SNPs for the patient and assessing whether the subject has an increased risk of incidence of prostate cancer when the determined genotype for one or more SNP in the selected SNP panel matches the genotype associated with PCSM.

Accordingly, the present disclosure provides kits and solutions for detecting one or more of the SNPs described herein. For example, the provided are kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a SNP-containing nucleic acid.

Kits can include, for instance, amplification reagents comprising primers sufficient to amplify at least one SNP that is predictive of PCSM and at least one probe for amplifying and detecting the polynucleotide sequence. In some embodiments, the kits further comprise a restriction enzyme for performing RFLP analysis. In addition, the kit can include nucleotides (e.g., A, C, G and T), a DNA polymerase, and appropriate buffers, salts and other reagents to facilitate amplification reactions.

These and other related embodiments may be better understood by reference to the following non-limiting examples.

EXAMPLES

Example 1

Association between Genetic Polymorphisms and Prostate Cancer Survival

This example describes the evaluation of the association between genetic polymorphisms and survival in prostate cancer patients.

A panel of 937 single nucleotide polymorphisms (SNPs) in 156 candidate genes associated with prostate cancer pathways of interest (e.g., androgens, estrogens, antioxidants, inflammation, DNA repair, and circadian rhythm) as well as SNPs identified in genome-wide association studies (GWAS) of prostate cancer were genotyped for 1,457 prostate cancer patients (mean follow-up=11.4 years; range 3-17 years; 90% Caucasian). For the present study, 1,309 Caucasian patients with available DNA were included.

Genomic DNA was extracted from peripheral blood using standard methods. Purified DNA was used to genotype SNPs on the Applied Biosystems (ABI; Foster City, Calif.) SNPlex system. SNP alleles were called by ABI's GeneMapper software. Each of these SNPs was evaluated for Hardy-Weinberg equilibrium (HWE) in a Caucasian control population that was age-matched to the 1,309 prostate cancer patient population cohort, and none were out of HWE (all p-values >0.05). Linkage disequilibrium was also evaluated between SNPs within the same gene. A total of 140 blind duplicate DNA samples were genotyped for each of the SNPs, with percent agreement ranging from 98.2% to 100% across all 22 SNPs. The average minor allele frequency for the 22 top SNPs was 23%, based on HapMap data for Caucasians.

Figure 2:
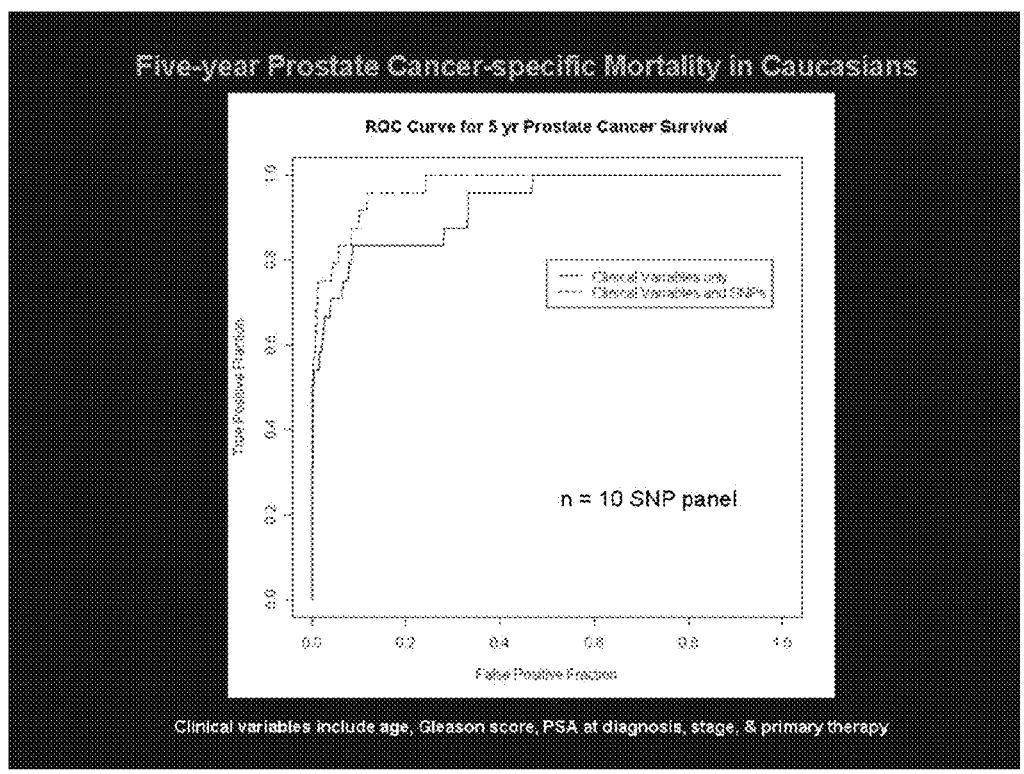
FIG. 2 is a graph depicting five-year prostate cancer-specific mortality in Caucasians.
Figure 3:
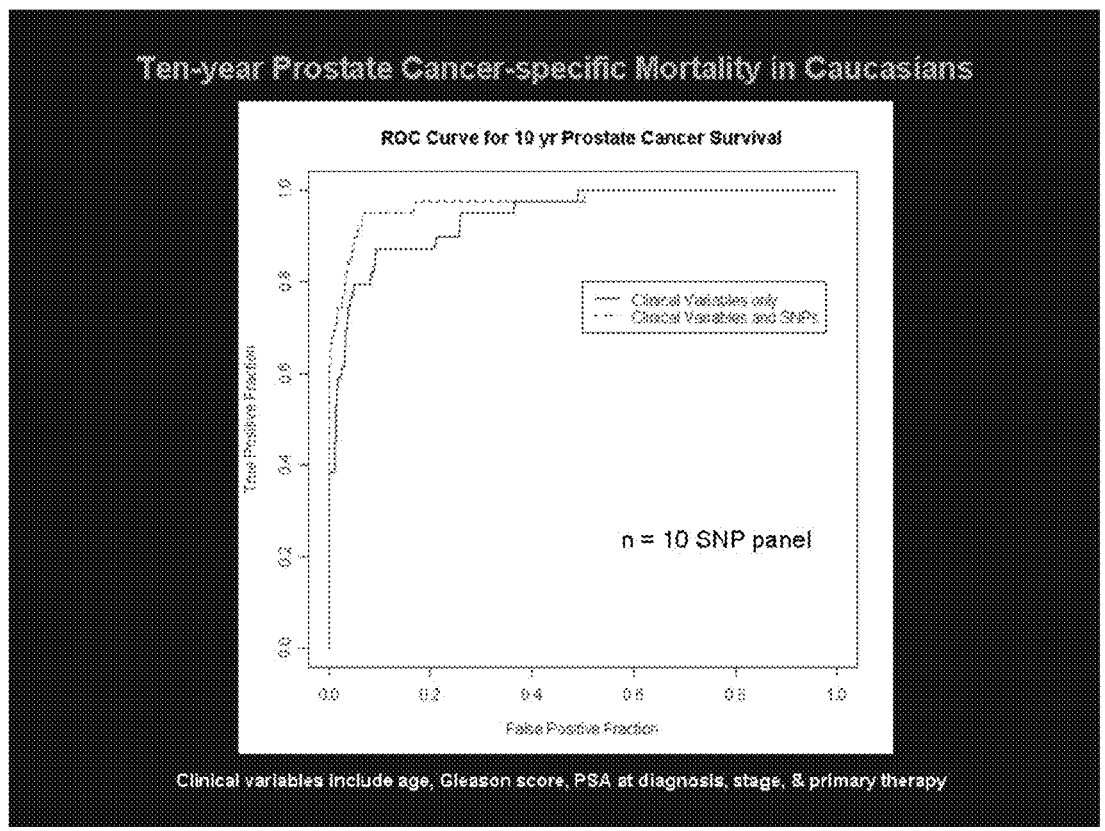
FIG. 3 is a graph depicting ten-year prostate cancer-specific mortality in Caucasians.
Figure 4A:
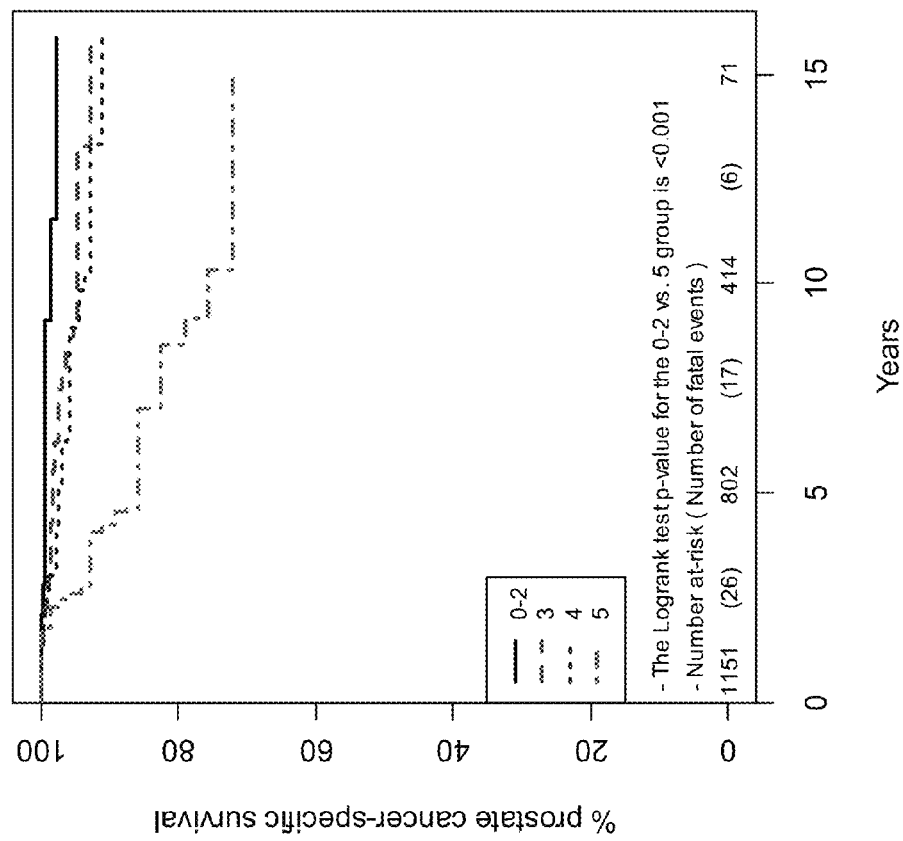
FIGS. 4A and 4B are Kaplan-Meier curves for prostate cancer-specific survival by number of at-risk genotypes for a 5 SNP panel in the Seattle cohort (FIG. 4A) and the Swedish cohort (FIG. 4B).
Figure 4B:
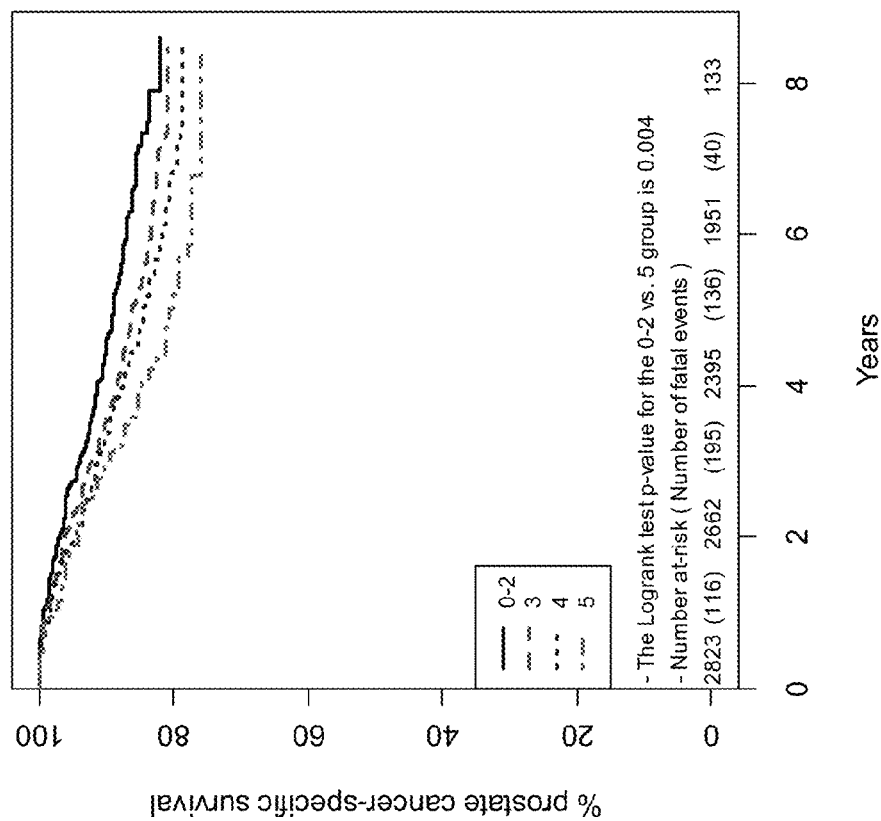

In preliminary analyses, a panel of 10 SNPs (p<0.001) was identified that appeared to be predictive of 5- and 10-year prostate-cancer mortality when the SNPs were added to a Cox regression model based on clinical variables (age, Gleason grade, clinical stage, diagnostic PSA, and primary therapy) (see FIGS. 1-3). The number of significant SNPs reaching the 0.001 significance level was much higher than the expected number by chance alone (846*0.001≈1). The over-fitting adjusted 5-year and 10-year prostate mortality receiver operator characteristic (ROC) curves were also produced using bootstrap re-sampling to estimate the optimism due to model fitting and subtracted from the ROC curves based on the regression model to get the "bias-adjusted ROC curve". These results support the contribution of germline gene variation to disease outcome.

In view of these findings, a panel of top SNPs was identified for validation in an independent cohort(s) of prostate cancer patients. A panel of SNPs was evaluated that contributed important information, beyond standard clinical features that are predictive of outcome. Thus, analyses were completed based on computing permutation p-values and associated False Discovery Rate estimates using two sets of models: (1) adjustment for age only, under a dominant genetic model, a trend (log-additive) model, and a best-fitting genetic model considering a dominant, recessive or trend model and (2) adjustment for age and clinical factors (Gleason score, stage at diagnosis, diagnostic PSA level, primary therapy) under the same three models described for the age-only models. A total of 1000 permutations were completed for each model. Based on the resulting data, a total of 22 top SNPs (p≤0.01 with a false discovery rate of ≤70%) were identified in relation to prostate cancer-specific death (Table 2).

TABLE 2

SNP Panel for Predicting Prostate Cancer Mortality

| Count | SNP | Location | Gene | Genotypes | Ref. allele | Assoc. allele (Risk of Disease) | MAF | Function | Call Rate | % Agree. |
|---|---|---|---|---|---|---|---|---|---|---|
| 1 | rs1137100 | 1p31.3 | LEPR | AA, AG, GG | A | G | 34% | coding, ns | 99.6 | 99.30% |
| 2 | rs228697 | 1p36.23 | PER3 | CC, CG, GG | C | G | 5% | coding, ns | 99.7 | 100% |
| 3 | rs2839685 | 10q11.21 | CXCL12 | CC, CT, TT | C | T | 15% | intergenic | 95.6 | 100% |
| 4 | rs1799814 | 15q24.1 | CYP1A1 | AA, AC, CC | C | A | 3% | coding, ns | 99.6 | 100% |
| 5 | rs627839 | 1q25.3 | RNASEL | GG, GT, TT | G | T | 46% | near gene 3 | 99.4 | 100% |
| 6 | rs5993891 | 22q11.21 | COMT/ARVCF | CC, CT, TT | C | T | 8% | intron | 99.9 | 100% |
| 7 | rs635261 | 1q25.3 | RNASEL | CC, CG, GG | G | C | 36% | intergenic | 99.5 | 100% |
| 8* | rs11710277 | 3p21.31 | SEMA3F | AA, AG, GG | A | G | 8% | intron | 97.4 | 98.20% |
| 9 | rs11205 | 5q23.1 | HSD17B4 | AA, AG, GG | A | G | 47% | coding, ns | 97.8 | 100% |
| 10 | rs2494750 | 14q32.33 | AKT1 | CC, CG, GG | C | G | 9% | intergenic | 99.1 | 99% |

TABLE 2-continued

SNP Panel for Predicting Prostate Cancer Mortality

| Count | SNP | Location | Gene | Genotypes | Ref. allele | Assoc. allele (Risk of Disease) | MAF | Function | Call Rate | % Agree. |
|---|---|---|---|---|---|---|---|---|---|---|
| 11 | rs4608577 | 2p21 | MSH2 | GG, GT, TT | T | G | 23% | intron | 99 | 100% |
| 12 | rs4645959 | 8q24.21 | MYC/8q24 | AA, AG, GG | A | G | 4% | coding, ns | 99.8 | 100% |
| 13 | rs1799964 | 6p21.33 | TNF/LTA | TT, TC, CC | T | C | 21% | near gene 3 | 99.6 | 99.30% |
| 14 | rs25487 | 19q13.31 | XRCC1 | AA, AG, GG | G | A | 36% | coding, ns | 99.6 | 100% |
| 15 | rs2308327 | 10q26.3 | MGMT | AA, AG, GG | A | G | 1% | coding, ns | 99.1 | 100% |
| 16 | rs915927 | 19q13.31 | XRCC1 | AA, AG, GG | A | G | 43% | coding, syn | 99.8 | 100% |
| 17 | rs2070874 | 5q31.1 | IL4 | CC, CT, TT | C | T | 16% | utr-5 | 99.4 | 98.50% |
| 18** | rs1029153 | 10q11.21 | CXCL12 | CC, CT, TT | T | C | 34% | utr-3 | 99.9 | 100% |
| 19 | rs12467911 | 2p23.1 | SRD5A2 | CC, CT, TT | C | T | 19% | intron | 99.1 | 100% |
| 20 | rs10778534 | 12q23.3 | CRY1 | TT, TC, CC | T | C | 42% | intergenic | 98.7 | 100% |
| 21 | rs523349 | 2p23.1 | SRD5A2 | CC, CG, GG | C | G | 19% | coding, syn | 98.9 | 100% |
| 22 | rs4583514 | 2p21 | MSH2 | AA, AG, GG | G | A | 45% | intron | 99.6 | 100% |

MAF = Minor allele frequency in HapMap-CEU
% Agree. = Agreement between 140 blind duplicate DNA samples
*HIM only;
**PROS only
Further description of each of these SNPs and their corresponding genes may be found at http://www.snpedia.com/index.php/SNPedia This panel of 22 top SNPs, identified in the Seattle Caucasian patient cohort (n=1,309), was used for biomarker validation, which involved genotyping prostate cancer patients from the Swedish CAPS study (2,875 patients, 501 prostate cancer-specific deaths). A panel of SNPs was confirmed by the independent CAPS dataset as predictive for prostate cancer-specific mortality in Caucasian men, after accounting for standard clinical factors known to influence mortality (i.e., age at diagnosis, Gleason score, stage of disease at diagnosis, diagnostic PSA level, and primary therapy).

ROC curves were generated to evaluate the contribution of the SNP panel genotypes to improving prediction of prostate cancer-specific survival compared to the prediction model based on clinical factors alone. In addition, ROC curves were generated to evaluate the SNP panel in predicting outcome when clinical variables are not included. Through this latter approach, it was determined whether the SNP panel results correlated with clinical features of disease.

As secondary goals, the following may also be evaluated: (1) the relationship between SNP genotypes and clinical characteristics such as Gleason score, stage of disease, and diagnostic PSA level and (2) the performance of the SNP panel in patient subgroups stratified by primary therapy (i.e., patients treated with curative intent—radical prostatectomy or radiation therapy).

The results of these studies reveal the relationship between genetic pathways and molecular mechanisms that determine metastatic potential and that push prostate cancer toward its lethal phenotype and help identify the subset of prostate cancer patients (a) at higher risk for adverse outcomes, (b) that benefit most from tailored individual therapies, (c) requiring heightened surveillance for disease recurrence/progression, and (d) susceptible to early interventions aimed at reducing prostate cancer morbidity and mortality.

Example 2

Study Subjects

Seattle Patient Cohort

The Seattle cohort was established from two prior population-based case-control studies of prostate cancer in residents of King County, Wash. Stanford et al., *Cancer Epidemiol. Biomarkers Prev.* 8(10):881-6 (1999); Agalliu et al., *Am. J. Epidemiol.* 168(3):250-60 (2008). In the first study, cases were diagnosed between Jan. 1, 1993, and Dec. 31, 1996 and were 40-64 years of age at diagnosis. In the second study, cases were diagnosed between Jan. 1, 2002, and Dec. 31, 2005 and were 35-74 years of age at diagnosis. Overall, 2,244 eligible prostate cancer patients were identified and 1,754 (78.2%) were interviewed. Blood samples yielding sufficient DNA for genotyping were drawn from 1,457 (83.1%) interviewed patients.

For the current study, 1,309 Caucasian patients with DNA available were included. These incident cases had histologically confirmed adenocarcinoma of the prostate and were ascertained from the Seattle-Puget Sound SEER cancer registry. The SEER registry provided information on Gleason score (i.e., tumor grade) Gleason DFTM (*Urologic Pathology: The Prostate* (Philadelphia: Lea and Febiger, 1977)) and cancer stage at diagnosis (i.e., localized, regional, or distant) defined according to the *American Joint Committee on Cancer Staging*, (Past Editions of the AJCC Cancer Staging Manual. (Chicago, 2010); available from: http://www.cancerstaging.org/products/pasteditions.html) diagnostic PSA level and primary therapy.

Young et al., *SEER Summary Staging Manual-2000: Codes and Coding Instructions* (Bethesda: National Cancer Institute, 2001). Vital status and cause of death were obtained through the SEER cancer registry, with death certificates obtained from the Washington State vital statistics office to verify the underlying cause of death. Prostate cancer was confirmed as the cause of death in 60 patients over an average follow-up period of 8.5 years (range 0.8-15.9 years); mortality status for this analysis was determined as of January 2009.

Swedish Patient Cohort

The validation cohort was comprised of patients enrolled in a Swedish population-based case-control study of prostate cancer. Zheng et al., *N. Engl. J. Med.* 358:910-19 (2008). Cases were recruited from four regions in Sweden through local Oncology Centers between July 2001 and October 2003. A total of 3,648 eligible patients were identified: 3,161 (87%) agreed to participate in the study interview and blood samples were obtained for 2,893 (92%) of those interviewed. For the current study, 2,875 patients of European descent had DNA available for genotyping. Information on clinicopathological factors was obtained from the National Prostate Cancer Register (Varenhorst et al., Scand. J. Urol. Nephrol. 39(2): 117-23 (2005)) including Gleason score, tumor stage, diagnostic PSA level and initial treatment. Follow-up for mortality as of June 2009 was based on record linkage to the Swedish Cause of Death Register (www.socialstyrelsen.se). Prostate cancer was confirmed as the underlying cause of death in 501 patients.

Example 3

Genotyping

Nine-hundred and thirty-seven SNPs primarily from candidate genes in biological pathways of interest for prostate cancer were genotyped in the Seattle cohort, using the SNPIex Genotyping System (Applied Biosystems, Inc., Foster City, Calif.). The GeneMapper software package (Applied Biosystems) was used to assign genotypes for each SNP. Replicate samples (n=140) were interspersed throughout all genotyping batches. Genotyping scores, including quality control data, were re-checked by different laboratory personnel and the accuracy of each assay was confirmed. Ninety SNPs were removed due to genotyping failure (N=57), monomorphism (N=27), or a minor allele frequency count of less than 10 (N=6). The remaining 847 SNPs were used for permutation testing to identify those associated with PCSM, after controlling for false-positive results.

Twenty-two SNPs were found to be significantly associated with PCSM in the Seattle cohort. For these SNPs, call rates were >95% and there was >98% agreement between duplicate samples. In addition, all 22 SNPs were in Hardy-Weinberg equilibrium (p>0.05) in 1,266 genotyped Caucasian controls who were age-matched to the Seattle patient cohort.

The 22 top ranking SNPs discovered in the Seattle cohort were selected for genotyping in the validation cohort. The MassARRAY iPLEX genotyping system (Sequenom) was used to genotype DNA samples at Wake Forest University. Duplicate samples and two negative controls that were blinded to the laboratory technician were included in each 96-well plate. Two SNPs (rs228697 and rs1029153) failed genotyping, leaving 20 SNPs for analysis in the validation component of the study.

Example 4

Statistical Analyses

SNP Selection by Permutation Testing

Six Cox regression models (three adjusting for age at diagnosis alone and three adjusting for age at diagnosis in addition to stage, Gleason score, diagnostic PSA, and primary treatment) were completed under dominant, recessive and log-additive (linear trend) genetic models. One-thousand permutation datasets were generated by randomly permuting all 847 SNPs together between subjects and the same six Cox models were run for each permuted dataset to obtain the distribution of p-values under the null hypothesis of no SNP effect, and to calculate the False Discovery Rate (FDR)[41] for different thresholds of selection by p-values in the original data. Twenty-two top ranked SNPs (p≤0.01 and FDR≤0.70) associated with PCSM from the six models were selected for validation.

Cox Models

The hazard ratio (HR), 95% confidence interval (CI) and p-value were obtained for each of the 22 top ranked SNPs (Seattle cohort), under the best-fitting genetic model (dominant, recessive or log-additive) for each SNP. Cox models using the same underlying best-fitting genetic model from the Seattle cohort, but allowing for three sets of covariates (i.e., 1) age at diagnosis; 2) age at diagnosis, Gleason score, stage, and diagnostic PSA level; and 3) age at diagnosis, Gleason score, stage, diagnostic PSA level and initial treatment), were completed for each of the 20 SNPs in the Swedish cohort and a SNP was judged to be validated if the p-value from either model was ≤0.05 (two-sided test). HRs for the cumulative number of at-risk genotypes were calculated by Cox models adjusted for age alone and for age plus the four clinicopathological factors (i.e., Gleason score, stage, PSA level, treatment). The grouping by number of at-risk genotypes was done to ensure that each group had an expected number of at least five fatal events given the prevalence of PCSM in the Seattle cohort. The same grouping of at-risk genotypes (i.e., 0-2, 3, 4, 5) was used to generate Kaplan-Meier curves. A backward stepwise Cox model (adjusted for age and the four clinicopathological factors) was used to rank validated SNPs by level of statistical significance. SNP by SNP interactions were also examined for all pairs of SNPs. An interaction effect was considered significant if the p-value associated with the HR was <0.001 (Bonferroni adjustment, p≤0.05).

Selected characteristics of the two patient cohorts are shown in Table 3. Patients in the Seattle cohort were younger at the time of prostate cancer diagnosis than those in the Swedish cohort (mean age at diagnosis 59.9 versus 65.8 years, respectively, p<0.0001). In addition, a higher proportion of patients from Sweden (17.4%) had died of prostate cancer relative to those from Seattle (4.6%) during a median follow-up time of 6.5 years in each cohort. Among patients who died of prostate cancer, those from Seattle had an earlier mean age at death (63.9 years) relative to those from Sweden (71.2 years), p<0.001. The Swedish population had a greater proportion of cases with more advanced stage, higher Gleason grade tumors and higher PSA levels at diagnosis. The distribution of primary treatment also varied by cohort, with a higher percentage of the Swedish patients either being treated with androgen deprivation therapy or remaining under surveillance with no initial treatment.

TABLE 3

Clinical and Pathological Characteristics of Two Prostate Cancer Patient Cohorts

| | Seattle (N = 1,309) | | Sweden (N = 2,875) | |
|---|---|---|---|---|
| | N | % | N | % |
| Age at diagnosis, years | | | | |
| Mean | 59.9 | | 65.8 | |
| Median | 60.0 | | 64.9 | |
| Range | 35.0-74.0 | | 44.6-80.4 | |
| Follow-up time, years | | | | |
| Mean | 8.5 | | 6.0 | |
| Median | 6.5 | | 6.5 | |
| Range | 0.8-15.9 | | 0.3-8.6 | |
| Prostate cancer-specific death | | | | |
| No† | 1,249 | 95.4 | 2,374 | 82.6 |
| Yes | 60 | 4.6 | 501 | 17.4 |
| Age at death, years | | | | |
| Mean | 63.9 | | 71.2 | |
| Median | 65.2 | | 71.2 | |
| Range | 44.9-78.3 | | 48.5-85.7 | |
| Stage | | | | |
| Local | 1,023 | 78.2 | 1,885 | 65.6 |
| Regional | 254 | 19.4 | 651 | 22.6 |
| Distant | 32 | 2.4 | 266 | 9.3 |
| Missing | 0 | 0.0 | 73 | 2.5 |

TABLE 3-continued

Clinical and Pathological Characteristics of Two Prostate Cancer Patient Cohorts

|  | Seattle (N = 1,309) | | Sweden (N = 2,875) | |
|---|---|---|---|---|
|  | N | % | N | % |
| Gleason score | | | | |
| 2-4 | 67 | 5.1 | 106 | 3.7 |
| 5-6 | 680 | 51.9 | 1,269 | 44.1 |
| 7 | 432 | 33.0 | 782 | 27.2 |
| 8-10 | 126 | 9.6 | 467 | 16.2 |
| Missing | 4 | 0.3 | 251 | 8.7 |
| Diagnostic PSA level, ng/mL | | | | |
| <4 | 178 | 13.6 | 148 | 5.1 |
| 4-9.9 | 722 | 55.2 | 993 | 34.5 |
| 10-19.9 | 191 | 14.6 | 651 | 22.6 |
| ≥20 | 118 | 9.0 | 1,003 | 34.9 |
| Missing | 100 | 7.6 | 80 | 2.8 |
| None | 115 | 8.8 | 488 | 17.0 |
| Other | 4 | 0.3 | 22 | 0.8 |
| Missing | 0 | 0.0 | 43 | 1.5 |

[†]Includes men who died of other causes and were censored at time of death (Seattle, n = 102; Sweden, n = 258)

Permutation testing on 847 SNPs revealed 22 sequence variants that were significantly (p≤0.01 and a FDR ≤0.70) associated with PCSM in the Seattle cohort (Table 4). As shown, the HRs for PSCM associated with these 22 genotypes in the Seattle cohort range from 0 to 0.49 for inverse associations and 2.0 to 28.2 for positive associations (p-values range from 0.01 to 0.0001) for this panel of markers, which were analyzed according to the best-fitting genetic model for each variant when adjusted for age at diagnosis alone or age plus the four clinicopathological factors.

TABLE 4

Hazard ratios (HR) for prostate cancer-specific mortality associated with a panel of 22 single nucleotide polymorphisms (SNPs) in candidate genes in a discovery cohort (Seattle) and a validation cohort (Sweden)*

| | | | | Seattle Cohort | | | | | Swedish Cohort | | | | |
|---|---|---|---|---|---|---|---|---|---|---|---|---|---|
| SNP | Chr. | Gene | Alleles[1] | MAF[2] | HR | 95% CI | P-value | Model[3] | MAF[2] | HR | 95% CI | P-value | Model[3] |
| rs1137100 | 1p31 | LEPR | A/G | 0.27 | 0.29 | 0.14-0.60 | 0.0001 | Dom: ACP | 0.29 | 0.82 | 0.67-1.00 | 0.05 | Dom: ACP |
| rs228697[†] | 1p36 | PER3 | C/G | 0.11 | 0.25 | 0.10-0.60 | 0.0002 | Dom: ACP | | | | | |
| rs635261 | 1q25 | RNASEL | G/C | 0.36 | 0.22 | 0.07-0.65 | 0.0007 | Rec: ACP | | | | | |
| rs627839 | 1q25 | RNASEL | G/T | 0.47 | 3.98 | 1.64-9.65 | 0.0004 | Dom: ACP | 0.47 | 1.22 | 1.00-1.50 | 0.05 | Dom: A |
| rs4583514 | 2p21 | MSH2 | G/A | 0.38 | 2.49 | 1.21-5.10 | 0.01 | Dom: ACP | | | | | |
| rs4608577 | 2p21 | MSH2 | T/G | 0.17 | 2.04 | 1.36-3.07 | 0.002 | Tre: A | | | | | |
| rs523349 | 2p23 | SRD5A2 | C/G | 0.29 | 0.49 | 0.28-0.86 | 0.01 | Dom: A | | | | | |
| rs12467911 | 2p23 | SRD5A2 | C/T | 0.28 | 0.45 | 0.24-0.81 | 0.005 | Dom: A | | | | | |
| rs11710277 | 3p21 | SEMA3F | A/G | 0.09 | 3.71 | 1.75-7.90 | 0.001 | Dom: ACP | | | | | |
| rs11205 | 5q23 | HSD17B4 | A/G | 0.39 | 0.21 | 0.06-0.70 | 0.001 | Rec: ACP | | | | | |
| rs2070874 | 5q31 | IL4 | C/T | 0.16 | 2.16 | 1.27-3.67 | 0.005 | Dom: A | 0.19 | 1.27 | 1.04-1.56 | 0.02 | Dom: ACP[4] |
| rs1799964 | 6p21 | TNF/LTA | T/C | 0.21 | 0.39 | 0.20-0.77 | 0.003 | Dom: A | | | | | |
| rs4645959 | 8q24 | C-MYC | A/G | 0.04 | 0 | 0.00-inf. | 0.003 | Tre: ACP | | | | | |
| rs1029153[†] | 10q11 | CXCL12 | T/C | 0.31 | 0.22 | 0.07-0.75 | 0.005 | Tre: A | | | | | |
| rs2839685 | 10q11 | CXCL12 | C/T | 0.15 | 28.2 | 7.21-110.2 | 0.0003 | Rec: ACP | | | | | |
| rs2308327 | 10q26 | MGMT | A/G | 0.13 | 0.32 | 0.13-0.78 | 0.004 | Tre: A | | | | | |
| rs10778534 | 12q23 | CRY1 | T/C | 0.36 | 2.21 | 1.19-4.12 | 0.008 | Dom: A | 0.35 | 1.23 | 1.00-1.51 | 0.04 | Tre: ACP |
| rs2494750 | 14q32 | AKT1 | C/G | 0.07 | 0.22 | 0.07-0.70 | 0.001 | Tre: ACP | | | | | |
| rs1799814 | 15q24 | CYP1A1 | C/A | 0.05 | 0.13 | 0.03-0.57 | 0.0003 | Tre: ACP | | | | | |
| rs25487 | 19q13 | XRCC1 | G/A | 0.36 | 0.49 | 0.31-0.77 | 0.003 | Tre: A | | | | | |
| rs915927 | 19q13 | XRCC1 | A/G | 0.43 | 2.54 | 1.24-5.18 | 0.005 | Dom: A | | | | | |
| rs5993891 | 22q11 | ARVCF | C/T | 0.05 | 0.21 | 0.07-0.61 | 0.0004 | Dom: ACP | 0.05 | 0.72 | 0.52-1.01 | 0.048 | Dom: A |

*Only data for the five validated SNPs are shown for the Swedish cohort.
[†]These SNPs were not evaluated in the Swedish cohort due to genotyping failure.
[1]Major/minor allele
[2]MAF: minor allele frequency calculated from cases that did not die from prostate cancer.
[3]Genetic model of best fit (Dom = dominant, Rec = recessive, Tre = trend) adjusted for age (A) alone, age + clinicopathological (ACP) factors (Gleason score, stage, diagnostic PSA level and primary treatment).
[4]Adjusted for age + clinicopathological factors as in footnote 3 above, excluding primary treatment.

TABLE 3-continued

Clinical and Pathological Characteristics of Two Prostate Cancer Patient Cohorts

|  | Seattle (N = 1,309) | | Sweden (N = 2,875) | |
|---|---|---|---|---|
|  | N | % | N | % |
| Primary therapy | | | | |
| Radical prostatectomy | 770 | 58.8 | 713 | 24.8 |
| Radiation therapy | 359 | 27.4 | 682 | 23.7 |
| Androgen deprivation | 61 | 4.7 | 927 | 32.2 |

Genotyping data from the Swedish cohort were available for 20 of these 22 SNPs and validated rs1137100 as being associated with PCSM (HR=0.82, 95% CI 0.67-1.00, p=0.05) in this patient population under the same dominant genetic model adjusted for the same covariates as in the Seattle dataset (i.e., age at diagnosis and the four clinicopathological factors). Also, under the same dominant genetic model as in the initial Seattle models but allowing for different covariates, four additional SNPs were validated as associated with PCSM in the Swedish cohort: rs2070874 (p=0.02), rs10778534 (p=0.04), rs5993891 (p=0.048), and rs627839 (p=0.05).

Hazard ratios were then calculated to assess the risk of PCSM by cumulative number of at-risk genotypes. As shown in Table 5 for the Swedish cohort, compared to men with 0-2 at-risk SNP genotypes, those with four (HR=1.5, 95% CI 1.2-2.0) or five (HR=1.5, 95% CI 1.0-2.2) at-risk genotypes had a 50% higher risk of dying from prostate cancer, after adjustment for age and clinicopathological factors. In the validation cohort, those with five at-risk genotypes had a 70% increased risk for PSCM when the model adjusted only for age at diagnosis. In both analyses, the HRs increased directly with the cumulative number (i.e., 0-2, 3, 4, 5) of at-risk genotypes (p-values for trend=0.0005, adjusting for age only, and =0.001 adjusting also for clinical and pathological factors). The proportion of all patients carrying four (28%) or five (6%) high-risk alleles was similar in both cohorts. The HRs also increased according to increasing number of at-risk genotypes in the Seattle cohort, although these estimates are less stable due to the smaller population with fewer fatal events. Of those men who died of prostate cancer, the median time to death for patients with 0-2 at-risk genotypes was 6.0 and 3.3 years, respectively for the Seattle and Swedish cohorts, whereas those with all five at-risk genotypes had a median time to death of 4.6 (Seattle) and 3.1 (Sweden) years.

TABLE 4

Hazard ratios (HR) for prostate cancer-specific mortality associated with the cumulative number of at-risk genotypes for a panel of five validated single nucleotide polymorphisms (SNPs)

| | | Seattle Cohort | | | | Swedish Cohort | | | | |
|---|---|---|---|---|---|---|---|---|---|---|
| No at-risk genotypes† | No. at-risk/ No. fatal events | HR‡ | 95% CI | HR§ | 95% CI | No. at-risk/ No. fatal events | HR‡ | 95% CI | HR§ | 95% CI |
| 0-2 | 314/4 | 1.00 | | 1.00 | | 803/113 | 1.00 | | 1.00 | |
| 3 | 446/16 | 2.82 | 0.94-8.45 | 8.14 | 2.44-27.12 | 1047/181 | 1.24 | 0.98-1.57 | 1.05 | 0.81-1.37 |
| 4 | 322/16 | 3.92 | 1.31-11.74 | 9.08 | 2.73-30.15 | 797/154 | 1.44 | 1.13-1.83 | 1.51 | 1.16-1.97 |
| 5 | 69/13 | 15.80 | 5.14-48.52 | 15.12 | 4.44-51.56 | 176/39 | 1.69 | 1.17-2.43 | 1.46 | 0.97-2.19 |

†Genotypes for SNPs rs1137100, rs627839, rs2070874, rs10778534, and rs5993891; patients missing data for any of the five SNP genotypes were excluded from the analysis (Seattle n = 158; Sweden n = 52).
‡Hazard ratio adjusted for age at diagnosis; p-value for trend = 0.0005 in the Swedish cohort.
§Hazard ratio adjusted for age at diagnosis, stage, Gleason score, diagnostic PSA, and primary treatment; p-value for trend = 0.001 in the Swedish cohort.

Kaplan-Meier (K-M) curves were constructed for PCSM according to the number of at-risk genotypes in each patient cohort (FIG. 1). In both datasets, PCSM increased with increasing number of at-risk SNP genotypes. As shown, compared to patients with 0-2 at-risk genotypes, those with all five of the at-risk SNP genotypes had the lowest prostate cancer-specific survival in both the Seattle (p<0.001) and the Swedish (p=0.004) cohorts.

Stepwise backward selection Cox models were completed to evaluate the relative ranking of these five confirmed SNP genotypes in relation to PCSM. Based on models adjusted for age at diagnosis and the four clinicopathological variables, the most significant SNP genotype in the Seattle dataset was for rs1137100 (p=0.001) in the LEPR gene and in the Swedish dataset was for rs10778534 (p=0.045) in the CRY1 gene.

Lastly, the five sequence variants were tested for SNP by SNP interactions. No evidence for significant interaction between these markers was found (all p-values for interaction >0.001).

What is claimed is:

1. A probe set for distinguishing between major and minor alleles for single-nucleotide polymorphisms (SNPs), said probe set comprising:
   (a) a first probe for distinguishing between major and minor alleles of SNP rs1137100 (SEQ ID NO: 1),
   (b) a second probe for distinguishing between major and minor alleles of SNP rs2070874 (SEQ ID NO: 17),
   (c) a third probe for distinguishing between major and minor alleles of SNP rs10778534 (SEQ ID NO: 20),
   (d) a fourth probe for distinguishing between major and minor alleles of SNP rs627839 (SEQ ID NO: 5), and
   (e) a fifth probe for distinguishing between major and minor alleles of SNP rs5993891 (SEQ ID NO: 6);
   wherein one or more of said probes is 15 to 30 nucleotides and wherein said probe set consists of between 5 and 44 probes, and wherein the probe set is fixed to a substrate.

2. The probe set of claim 1, further comprising one or more probes for distinguishing between major and minor alleles of one or more SNPs, wherein each of said one or more probes is selected from the group consisting of
   (f) a probe for distinguishing between major and minor alleles of SNP rs228697 (SEQ ID NO: 2),
   (g) a probe for distinguishing between major and minor alleles of SNP rs2839685 (SEQ ID NO: 3),
   (h) a probe for distinguishing between major and minor alleles of SNP rs1799814 (SEQ ID NO: 4),
   (i) a probe for distinguishing between major and minor alleles of SNP rs635261 (SEQ ID NO: 7),
   (j) a probe for distinguishing between major and minor alleles of SNP rs11710277 SEQ ID NO: 8),
   (k) a probe for distinguishing between major and minor alleles of SNP rs11205 (SEQ ID NO: 9),
   (l) a probe for distinguishing between major and minor alleles of SNP rs2494750 (SEQ ID NO: 10),
   (m) a probe for distinguishing between major and minor alleles of SNP rs4608577 (SEQ ID NO: 11),
   (n) a probe for distinguishing between major and minor alleles of SNP rs4645959 (SEQ ID NO: 12),
   (o) a probe for distinguishing between major and minor alleles of SNP rs1799964 (SEQ ID NO: 13),
   (p) a probe for distinguishing between major and minor alleles of SNP rs25487 (SEQ ID NO: 14),
   (q) a probe for distinguishing between major and minor alleles of SNP rs2308327 (SEQ ID NO: 15),
   (r) a probe for distinguishing between major and minor alleles of SNP rs915927 (SEQ ID NO: 16),
   (s) a probe for distinguishing between major and minor alleles of SNP rs1029153 (SEQ ID NO: 18),
   (t) a probe for distinguishing between major and minor alleles of SNP rs12467911 (SEQ ID NO: 19),
   (u) a probe for distinguishing between major and minor alleles of SNP rs523349 (SEQ ID NO: 21), and
   (v) a probe for distinguishing between major and minor alleles of SNP rs4583514 (SEQ ID NO: 22).

3. The probe set of claim 1, wherein said first probe hybridizes with a nucleic acid comprising the nucleotide sequence set forth in SEQ ID NO: 1, wherein the "n" at position 27 is "A", or the complement thereof, but does not hybridize under the same conditions of temperature and buffer with the nucleotide sequence set forth in SEQ ID NO: 1, wherein the n at position 27 is "G".

4. The probe set of claim 1, wherein said second probe hybridizes with a nucleic acid comprising the nucleotide sequence set forth in SEQ ID NO: 17, wherein the "n" at position 27 is "C", or the complement thereof, but does not hybridize under the same conditions of temperature and buffer with the nucleotide sequence set forth in SEQ ID NO: 17, wherein the n at position 27 is "T".

5. The probe set of claim 1, wherein said third probe hybridizes with a nucleic acid comprising the nucleotide sequence set forth in SEQ ID NO: 20, wherein the "n" at position 27 is "T", or the complement thereof, but does not hybridize under the same conditions of temperature and buffer with the nucleotide sequence set forth in SEQ ID NO: 20, wherein the n at position 27 is "C".

6. The probe set of claim 1, wherein said fourth probe hybridizes with a nucleic acid comprising the nucleotide sequence set forth in SEQ ID NO: 5, wherein the "n" at position 27 is "G", or the complement thereof, but does not hybridize under the same conditions of temperature and buffer with the nucleotide sequence set forth in SEQ ID NO: 5, wherein the n at position 27 is "T".

7. The probe set of claim 1, wherein said fifth probe hybridizes with a nucleic acid comprising the nucleotide sequence set forth in SEQ ID NO: 6, wherein the "n" at position 27 is "C", or the complement thereof, but does not hybridize under the same conditions of temperature and buffer with the nucleotide sequence set forth in SEQ ID NO: 1, wherein the n at position 27 is "T".

8. The probe set of claim 1, wherein said first probe comprises the nucleotide sequence g aaggaaAgac attt (nucleotides 20-34 of SEQ ID NO: 1, with an A at the "n" position) or the complement thereof.

9. The probe set of claim 1, wherein said second probe comprises the nucleotide sequence c taattgCctcacat acat (nucleotides 20-34 of SEQ ID NO: 17, with a C at the "n" position) or the complement thereof.

10. The probe set of claim 1, wherein said third probe comprises the nucleotide sequence g caattaTaag actc (nucleotides 20-34 of SEQ ID NO: 20, with a T at the "n" position) or the complement thereof.

11. The probe set of claim 1, wherein said fourth probe comprises the nucleotide sequence g aaggttGtgc tgtt (nucleotides 20-34 of SEQ ID NO: 5, with a G at the "n" position) or the complement thereof.

12. The probe set of claim 1, wherein said fifth probe comprises the nucleotide sequence t gtacctCacc ctct (nucleotides 20-34 of SEQ ID NO: 6, with a C at the "n" position) or the complement thereof.

* * * * *

SEQUENCE LISTING

<160> NUMBER OF SEQ ID NOS: 22

<210> SEQ ID NO 1
<211> LENGTH: 52
<212> TYPE: DNA
<213> ORGANISM: Homo sapiens
<220> FEATURE:
<221> NAME/KEY: misc_feature
<223> OTHER INFORMATION: SNP Identifier:  rs1137100
<220> FEATURE:
<221> NAME/KEY: misc_feature
<222> LOCATION: (27)..(27)
<223> OTHER INFORMATION: n is a (major allele) or g (minor allele)

<400> SEQUENCE: 1
cttatgtgca gacaacattg aaggaangac atttgtttca acagtaaatt ct        52

```
<210> SEQ ID NO 2
<211> LENGTH: 52
<212> TYPE: DNA
<213> ORGANISM: Homo sapiens
<220> FEATURE:
<221> NAME/KEY: misc_feature
<223> OTHER INFORMATION: SNP Identifier: rs228697
<220> FEATURE:
<221> NAME/KEY: misc_feature
<222> LOCATION: (27)..(27)
<223> OTHER INFORMATION: n is c (major allele) or g (minor allele)

<400> SEQUENCE: 2
ttatgaccgt tttcctgcct gacccnctg tctgtcctct gttgtcgcca tc        52

<210> SEQ ID NO 3
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs2839685
<220> FEATURE:
<221> NAME/KEY: misc_feature
<222> LOCATION: (27)..(27)
<223> OTHER INFORMATION: n is c (major allele) or t (minor allele)

<400> SEQUENCE: 3 aaagggcgc tctcctcacc cccacgnctc ctgggtgccg acctgcaccc tc         52

<210> SEQ ID NO 4
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs1799814
<220> FEATURE:
<221> NAME/KEY: misc_feature
<222> LOCATION: (27)..(27)
<223> OTHER INFORMATION: n is a (major allele) or c (minor allele)

<400> SEQUENCE: 4
gggcaagcgg aagtgtatcg gtgagancat tgcccgctgg gaggtctttc tc         52

<210> SEQ ID NO 5
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs627839
<220> FEATURE:
<221> NAME/KEY: misc_feature
<222> LOCATION: (27)..(27)
<223> OTHER INFORMATION: n is g (major allele) or t (minor allele)

<400> SEQUENCE: 5
cccagggtct cctccagagg aaggttntgc tgttctttac ccaaatcatc tt         52

<210> SEQ ID NO 6
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs5993891
<220> FEATURE:
<221> NAME/KEY: misc_feature
```

<222> LOCATION: (27)..(27)
<223> OTHER INFORMATION: n is c (major allele) or t (minor allele)

<400> SEQUENCE: 6
aatccctctc tagctgccct gtacctnacc ctctaagcac ccctaaacca aa        52

<210> SEQ ID NO 7
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs635261
<220> FEATURE:
<221> NAME/KEY: misc_feature
<222> LOCATION: (27)..(27)
<223> OTHER INFORMATION: n is c (major allele) or g (minor allele)

<400> SEQUENCE: 7
tgtcccaaat gaaactcttg gtcttcnctc taaacctgct cctctggaag cc        52

<210> SEQ ID NO 8
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs11710277
<220> FEATURE:
<221> NAME/KEY: misc_feature
<222> LOCATION: (27)..(27)
<223> OTHER INFORMATION: n is a (major allele) or g (minor allele)

<400> SEQUENCE: 8
tgggcacccc agccaggtct agagccngaa gggtgtgagg gtcaagcagc cc        52

<210> SEQ ID NO 9
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs11205
<220> FEATURE:
<221> NAME/KEY: misc_feature
<222> LOCATION: (27)..(27)
<223> OTHER INFORMATION: n is a (major allele) or g (minor allele)

<400> SEQUENCE: 9
ataatgatgt gtcaagattc aaggcantta aggtaaatgt gtattactac gt        52

<210> SEQ ID NO 10
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs2494750
<220> FEATURE:
<221> NAME/KEY: misc_feature
<222> LOCATION: (27)..(27)
<223> OTHER INFORMATION: n is c (major allele) or g (minor allele)

<400> SEQUENCE: 10
cccctttctc ctggacactc acagganagt gcaggtgact gccaccccga cc        52

<210> SEQ ID NO 11
<211> LENGTH: 52
<212> TYPE: DNA

```
<213> ORGANISM: Homo sapiens
<220> FEATURE:
<221> NAME/KEY: misc_feature
<223> OTHER INFORMATION: SNP identifier: rs4608577
<220> FEATURE:
<221> NAME/KEY: misc_feature
<222> LOCATION: (27)..(27)
<223> OTHER INFORMATION: n is g (major allele) or t (minor allele)

<400> SEQUENCE: 11
accttataaa tctccactac catgttnttg cttggactgt tcacacttcc tg            52

<210> SEQ ID NO 12
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs4645959
<220> FEATURE:
<221> NAME/KEY: misc_feature
<222> LOCATION: (27)..(27)
<223> OTHER INFORMATION: n is a (major allele) or g (minor allele)

<400> SEQUENCE: 12
cctcaacgtt agcttcacca acaggancta tgacctcgac tacgactcgg tg            52

<210> SEQ ID NO 13
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs1799964
<220> FEATURE:
<221> NAME/KEY: misc_feature
<222> LOCATION: (27)..(27)
<223> OTHER INFORMATION: n is c (major allele) or t (minor allele)

<400> SEQUENCE: 13
gggaagcaaa ggagaagctg agaagangaa ggaaaagtca gggtctggag gg            52

<210> SEQ ID NO 14
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs25487
<220> FEATURE:
<221> NAME/KEY: misc_feature
<222> LOCATION: (27)..(27)
<223> OTHER INFORMATION: n is a (major allele) or g (minor allele)

<400> SEQUENCE: 14
ccgcatgcgt cggcggctgc cctcccngag gtaaggcctc acacgccaac cc            52

<210> SEQ ID NO 15
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs2308327
<220> FEATURE:
<221> NAME/KEY: misc_feature
<222> LOCATION: (27)..(27)
<223> OTHER INFORMATION: n is a (major allele) or g (minor allele)

<400> SEQUENCE: 15
```
ggcccatgaa ggccaccggt tggggangcc aggcttggga gggagctcag gt    52

<210> SEQ ID NO 16
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs915927
<220> FEATURE:
<221> NAME/KEY: misc_feature
<222> LOCATION: (27)..(27)
<223> OTHER INFORMATION: n is a (major allele) or g (minor allele)

<400> SEQUENCE: 16
cccttcatag tcacagccag cgacccngca ggacctagct atgcagctgc ta    52

<210> SEQ ID NO 17
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs2070874
<220> FEATURE:
<221> NAME/KEY: misc_feature
<222> LOCATION: (27)..(27)
<223> OTHER INFORMATION: n is c (major allele) or t (minor allele)

<400> SEQUENCE: 17
gttagcttct cctgataaac taattgnctc acattgtcac tgcaaatcga ca    52

<210> SEQ ID NO 18
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs1029153
<220> FEATURE:
<221> NAME/KEY: misc_feature
<222> LOCATION: (27)..(27)
<223> OTHER INFORMATION: n is c (major allele) or t (minor allele)

<400> SEQUENCE: 18
aggaagtagg aagtaaatta tagtgangta atcttgaatt gtaactgttc tt    52

<210> SEQ ID NO 19
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs12467911
<220> FEATURE:
<221> NAME/KEY: misc_feature
<222> LOCATION: (27)..(27)
<223> OTHER INFORMATION: n is c (major allele) or t (minor allele)

<400> SEQUENCE: 19
gtctggatat ctgtgaccta gaaatcngga gtacagcacc ctgggggctc tt    52

<210> SEQ ID NO 20
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier: rs10778534
<220> FEATURE:

```
<221> NAME/KEY: misc_feature
<222> LOCATION: (27)..(27)
<223> OTHER INFORMATION: n is c (major allele) or t (minor allele)

<400> SEQUENCE: 20
acatggacat gggagtcctg caattanaag actccaagaa ggccatatga ct            52

<210> SEQ ID NO 21
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier:  rs523349
<220> FEATURE:
<221> NAME/KEY: misc_feature
<222> LOCATION: (27)..(27)
<223> OTHER INFORMATION: n is c (major allele) or g (minor allele)

<400> SEQUENCE: 21
aaaacgctac ctgtggaagt aatgtangca gaagaggccc agaagtaccg tc            52

<210> SEQ ID NO 22
<211> LENGTH: 52
<212> TYPE: DNA
<213> ORGANISM: Homo sapiens
<220> FEATURE:
<221> NAME/KEY: misc_feature
<223> OTHER INFORMATION: SNP identifier:  rs4583514
<220> FEATURE:
<221> NAME/KEY: misc_feature
<222> LOCATION: (27)..(27)
<223> OTHER INFORMATION: n is a (major allele) or g (minor allele)

<400> SEQUENCE: 22
gtattgtctt aaaagagtga ttgatgntag ctacggaaaa ctttgatttt ta            52
```